United States Patent
Yamaoka et al.

(10) Patent No.: US 12,023,437 B2
(45) Date of Patent: Jul. 2, 2024

(54) INSUFFLATION SYSTEM AND INSUFFLATION CONTROL METHOD

(71) Applicant: OLYMPUS CORPORATION, Tokyo (JP)

(72) Inventors: Koji Yamaoka, Hamura (JP); Yuma Kasuya, Fuchu (JP); Shinya Torii, Tokyo (JP); Keita Kimura, Hachioji (JP); Kunitoshi Hiraga, Tama (JP); Takefumi Uesugi, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 325 days.

(21) Appl. No.: 17/337,617

(22) Filed: Jun. 3, 2021

(65) Prior Publication Data
US 2021/0290864 A1 Sep. 23, 2021

Related U.S. Application Data

(63) Continuation of application No. PCT/JP2018/044689, filed on Dec. 5, 2018.

(51) Int. Cl.
*A61M 13/00* (2006.01)

(52) U.S. Cl.
CPC ... *A61M 13/003* (2013.01); *A61M 2202/0225* (2013.01); *A61M 2205/3334* (2013.01); *A61M 2205/3337* (2013.01); *A61M 2205/50* (2013.01)

(58) Field of Classification Search
CPC ........ A61M 13/003; A61M 2202/0225; A61M 2205/3334; A61M 2205/3337;
(Continued)

(56) References Cited

U.S. PATENT DOCUMENTS 6,402,714 B1 * 6/2002 Kraft-Kivikoski .......................... A61M 13/003
604/23
2004/0034339 A1 * 2/2004 Stoller ................. A61B 1/3132
606/1

(Continued)

FOREIGN PATENT DOCUMENTS

JP H05-329164 A 12/1993
JP H09-94252 A 4/1997
(Continued)

OTHER PUBLICATIONS

International Search Report dated Feb. 19, 2019 issued in PCT/JP2018/044689.

*Primary Examiner* — Kami A Bosworth
*Assistant Examiner* — Avery Smale
(74) *Attorney, Agent, or Firm* — Scully, Scott, Murphy & Presser, P.C.

(57) ABSTRACT

An insufflation system having a processor configured to calculate a first target gas feeding flow rate based on a difference between a body cavity internal pressure and an insufflation target pressure of a body cavity, determine whether the first target gas feeding flow rate is lower than a threshold gas feeding flow rate, and in response to determining that the first target gas feeding flow rate is lower than the threshold gas feeding flow rate, feed gas at a second target gas feeding flow rate by controlling a first valve provided at a gas feeding conduit and a second valve provided at a suction conduit, wherein the processor is configured to cause the suction conduit to suction at a first suction flow rate, and wherein the second target gas feeding flow rate is obtained by adding the first suction flow rate to the first target gas feeding flow rate.

17 Claims, 21 Drawing Sheets

(58) Field of Classification Search
CPC .............. A61M 2205/50; A61M 13/00; A61M 13/006; A61M 2205/3331; A61M 2205/3341; A61M 2205/3344
See application file for complete search history.

(56) References Cited

U.S. PATENT DOCUMENTS

| | | | |
|---|---|---|---|
| 2009/0221963 A1* | 9/2009 | Lloyd | A61B 18/20 604/119 |
| 2015/0367087 A1* | 12/2015 | Dor Zidon | B01J 7/00 604/26 |
| 2016/0106934 A1* | 4/2016 | Hiraga | A61B 1/3132 604/26 |
| 2018/0221598 A1* | 8/2018 | Silver | A61M 13/006 |
| 2018/0280634 A1 | 10/2018 | O'Dea | |

FOREIGN PATENT DOCUMENTS

| | | |
|---|---|---|
| JP | H11-332825 A | 12/1999 |
| JP | 4363693 B2 | 11/2009 |
| JP | 2017-502703 A | 1/2017 |
| WO | 2016/071893 A1 | 5/2016 |
| WO | WO-2018173044 A1 * | 9/2018 ............... A61B 1/31 |

* cited by examiner

INSUFFLATION SYSTEM AND INSUFFLATION CONTROL METHOD

CROSS REFERENCE TO RELATED APPLICATION

This application is a continuation application of PCT/JP2018/044689 filed on Dec. 5, 2018, the entire contents of which are incorporated herein by this reference.

BACKGROUND OF THE INVENTION

1. Field of the Invention

The present invention relates to an insufflation system and an insufflation control method.

2. Description of the Related Art

Recently, a laparoscopic surgical operation that performs medical treatment without laparotomy has been performed to reduce invasion to a patient. In the laparoscopic surgical operation, the abdominal region of the patient is punctured by, for example, a first trocar that guides an observation endoscope into the body cavity, and a second trocar that guides a treatment instrument to a treatment site. In the laparoscopic surgical operation, treatment and the like are performed by using the endoscope inserted into the abdominal cavity through an insertion hole of the first trocar while the treatment site and the treatment instrument inserted through an insertion hole of the second trocar are being observed.

In such a laparoscopic surgical operation, an insufflation device is used to ensure the visual field of the endoscope and ensure a region in which the treatment instrument is operated. The insufflation device expands inside of the body cavity to a constant pressure by injecting, for example, carbon dioxide gas as insufflation gas into the cavity, thereby ensuring the visual field of the endoscope and the operation region of the treatment instrument.

Conventionally, the insufflation device has been often used to expand the abdominal cavity by feeding two to three liters of gas. However, recently, the insufflation device has been increasingly used to expand not only the abdominal cavity but also various sites such as the retroperitoneal space, the chest cavity, the subcutaneous space, the rectum, and the large intestine. The volume of an insufflation site is different depending on an expansion target site and a procedure, and thus the amount of gas feeding is different. For example, the amount of gas feeding is 100 milliliter approximately when the rectum is swelled in transanal total mesorectal excision (TaTME).

When such a small volume cavity is expanded, it is important to reliably control the insufflation device from a minute flow rate to a high flow rate in accordance with the size of the cavity. For example, Japanese Patent No. 4363693 discloses an insufflation system configured to reliably perform flow rate control.

SUMMARY OF THE INVENTION

An insufflation system according to an aspect of the present invention includes: an insufflation device communicating with a gas feeding source configured to feed predetermined gas, the insufflation device being configured to supply the gas into a body cavity of a subject through a gas feeding conduit; and a suction device configured to suction the gas from the body cavity at a predetermined suction flow rate and discharge the gas out of the body cavity through a suction conduit. The insufflation device includes a flow rate sensor configured to measure a gas feeding flow rate of the gas, a pressure sensor configured to measure body cavity internal pressure of the subject, a first on-off valve provided on the gas feeding conduit and configured to control the gas feeding flow rate of the gas, a second on-off valve provided on the suction conduit and configured to control opening and closing of the suction conduit, and a processor configured to calculate a first target gas feeding flow rate of the gas from a difference between the body cavity internal pressure and insufflation target pressure of the body cavity and configured to open the second on-off valve and control the first on-off valve to feed the gas at a second target gas feeding flow rate when the first target gas feeding flow rate is lower than a threshold gas feeding flow rate set in advance, the second target gas feeding flow rate being obtained by adding the suction flow rate to the first target gas feeding flow rate.

An insufflation control method according to an aspect of the present invention is an insufflation control method using an insufflation system. The insufflation system includes: an insufflation device communicating with a gas feeding source configured to feed predetermined gas, the insufflation device being configured to supply the gas into a body cavity of a subject through a gas feeding conduit; and a suction device configured to suction the gas from the body cavity at a predetermined suction flow rate and discharge the gas out of the body cavity through a suction conduit. The insufflation control method includes: measuring a gas feeding flow rate of the gas; measuring body cavity internal pressure of the subject; calculating a first target gas feeding flow rate of the gas from a difference between the body cavity internal pressure and insufflation target pressure of the body cavity; and opening a second on-off valve and controlling a first on-off valve to feed the gas at a second target gas feeding flow rate when the first target gas feeding flow rate is lower than a threshold gas feeding flow rate set in advance, the first on-off valve being provided on the gas feeding conduit and configured to control the gas feeding flow rate of the gas, the second on-off valve being provided on the suction conduit and configured to control opening and closing of the suction conduit, the second target gas feeding flow rate being obtained by adding the suction flow rate to the first target gas feeding flow rate.

DETAILED DESCRIPTION OF THE PREFERRED EMBODIMENTS

Embodiments of the present invention will be described below with reference to the accompanying drawings.

First Embodiment

Figure 1:
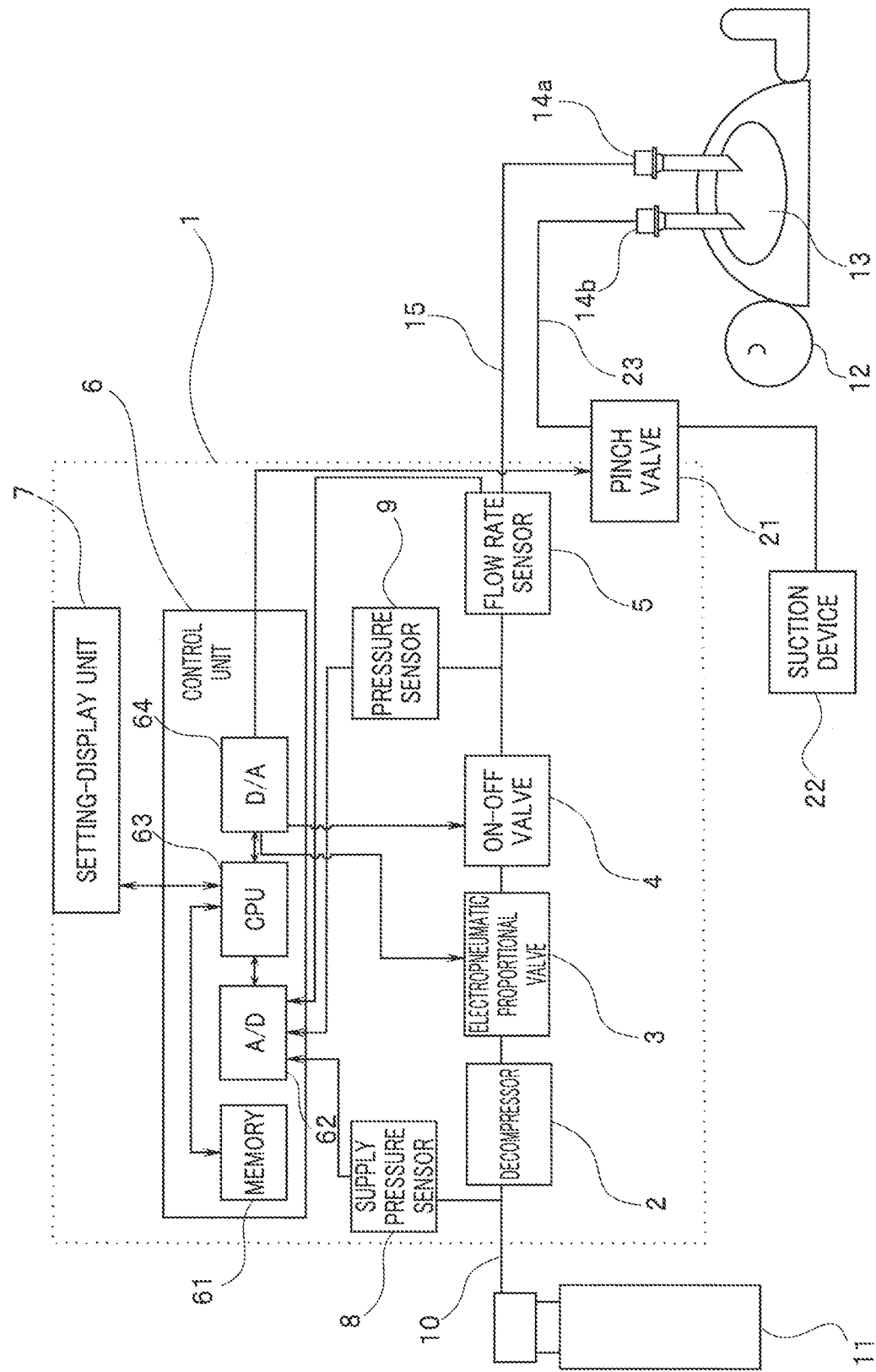
FIG. 1 is a diagram illustrating an exemplary entire configuration of an insufflation system according to an embodiment of the present invention.

FIG. 1 is a diagram for description of an exemplary entire configuration of an insufflation system according to an embodiment of the present invention. As illustrated in FIG. 1, the insufflation system according to the present embodiment includes an insufflation device 1 and a suction device 22. The insufflation device 1 mainly includes a decompressor 2, an electropneumatic proportional valve 3 (first on-off valve), an on-off valve 4, a flow rate sensor 5, a supply pressure sensor 8, a pressure sensor 9, a control unit 6, a setting-display unit 7, and a pinch valve 21 (second on-off valve, pinch valve).

The insufflation device 1 is connected with a gas supply source 11 (gas feeding source) (for example, a carbon dioxide gas cylinder) through a high-pressure gas tube 10. The insufflation device 1 is also connected with a gas feeding tube 15 as a gas feeding conduit for feeding insufflation gas such as carbon dioxide gas into an abdominal cavity 13 (body cavity) of a patient 12 (subject) through a trocar 14a inserted into the body cavity. FIG. 1 illustrates an example in which the abdominal cavity 13 is an insufflation target site, but the insufflation target site may be another site such as the retroperitoneal space, the chest cavity, the subcutaneous space, the rectum, or the large intestine. The trocar 14a is inserted into the insufflation target site.

The decompressor 2 depressurizes high-pressure gas supplied from the gas supply source 11 to pressure that is harmless to the human body. For example, gas supplied from the gas supply source 11 at a high pressure of 6 MPa approximately is depressurized to 50 to 80 mmHg approximately.

The electropneumatic proportional valve 3 is an electrically driven valve and can adjust gas feeding pressure to a predetermined pressure value by changing decompression spring force acting on a valve part to electrically adjust the opening degree of the valve part at multiple stages. The opening degree of the valve is adjusted by adjusting the amount of current applied to the valve based on a control signal inputted from the control unit 6 so that the pressure of carbon dioxide gas depressurized by the decompressor 2 changes to gas feeding pressure in the range of 0 to 80 mmHg approximately.

The on-off valve 4 can feed gas into the gas feeding conduit and stop the feeding by switching opening and closing of a valve part based on a control signal inputted from the control unit 6.

The supply pressure sensor 8 measures pressure in the gas feeding conduit. The pressure measurement is performed at gas supply. The pressure of gas supplied from the gas supply source 11 is measured and a result of the measurement is outputted to the control unit 6.

The pressure sensor 9 measures the pressure (body cavity internal pressure) of the abdominal cavity 13 through the gas feeding tube 15. The pressure measurement is performed during gas feeding stopping. A result of the measurement by the pressure sensor 9 is outputted to the control unit 6.

The flow rate sensor 5 measures the flow rate (gas feeding flow rate) of carbon dioxide gas supplied into the body cavity and outputs a result of the measurement to the control unit 6.

The gas feeding tube 15 is a tube through which gas sent from the insufflation device 1 is guided to the trocar 14a. Typically, the tube is formed of flexible material and has a length of 3 m approximately.

The control unit 6 as a determination unit and a display control unit controls each unit in the insufflation device 1. The control unit 6 mainly includes a memory 61, an analog/digital converter (hereinafter abbreviated as A/D) 62, a CPU 63, and a digital/analog converter (hereinafter abbreviated as D/A) 64. The control unit 6 functions as each unit in the control unit 6 when a processor including the CPU 63 or the like executes software stored in the memory 61. However, the present invention is not limited to this configuration, but the control unit 6 may be constituted by a processor including an electronic circuit corresponding to each unit in the control unit 6 or may be constituted by a processor including an integrated circuit such as a field programmable gate array (FPGA) including a circuit unit corresponding to each unit in the control unit 6.

The memory 61 stores, for example, various set values such as supply pressure, intraluminal pressure, and the flow rate, a lowest flow rate $F_{min}$ that is controllable by the electropneumatic proportional valve 3, and a suction flow rate $F_{asp}$ of the suction device 22. Normally, the lowest flow rate $F_{min}$ to which control is possible by the electropneumatic proportional valve 3 is a value equal to approximately 10% of a maximum flow rate. For example, the lowest flow rate $F_{min}$ is 5 L/min when the maximum flow rate is 50 L/min. In addition, the memory 61 stores various kinds of information related to screens, such as screen patterns to be displayed on the setting-display unit 7 and display patterns of warning messages.

The A/D 62 reads data (analog value) measured by each of the supply pressure sensor 8, the pressure sensor 9, and the flow rate sensor 5, converts the data into a digital value, and outputs the digital value to the CPU 63.

The CPU 63 reads various set values stored in the memory 61 and collates the set values to measurement data inputted from the A/D 62. The opening degree of the electropneumatic proportional valve 3 and opening and closing of the pinch valve 21 are set based on a result of the collation so that the supply pressure and the flow rate have optimum values. The set values are outputted to the D/A 64.

The D/A 64 controls the opening degree of the electropneumatic proportional valve 3 and opening and closing of the pinch valve 21 in accordance with the set values inputted from the CPU 63.

The setting-display unit 7 is provided on a front panel of the insufflation device 1 and displays an appropriate screen in accordance with an instruction from the CPU 63. Normally, the front panel can receive inputting from a user by a touch panel scheme. Contents inputted from the user such as various set values are outputted from the setting-display unit 7 to the CPU 63. The CPU 63 changes, in accordance with the inputted contents, a screen to be displayed by the setting-display unit 7 and various set values stored in the memory 61.

The suction device 22 is connected with a suction tube 23 as a suction conduit for suctioning gas that fills the body cavity through a trocar 14b inserted into the abdominal cavity 13 of the patient 12. The pinch valve 21 is installed halfway through the suction tube 23. In the present embodiment, the suction device 22 does not have a function to adjust the suction flow rate, and the suction flow rate $F_{asp}$ is a fixed value. For example, the suction flow rate $F_{asp}$ is 12 L/min approximately.

The pinch valve 21 opens and closes a flow path by pinching the suction tube 23. The flow path opening and closing are performed based on a control signal inputted from the control unit 6.

Figure 2:
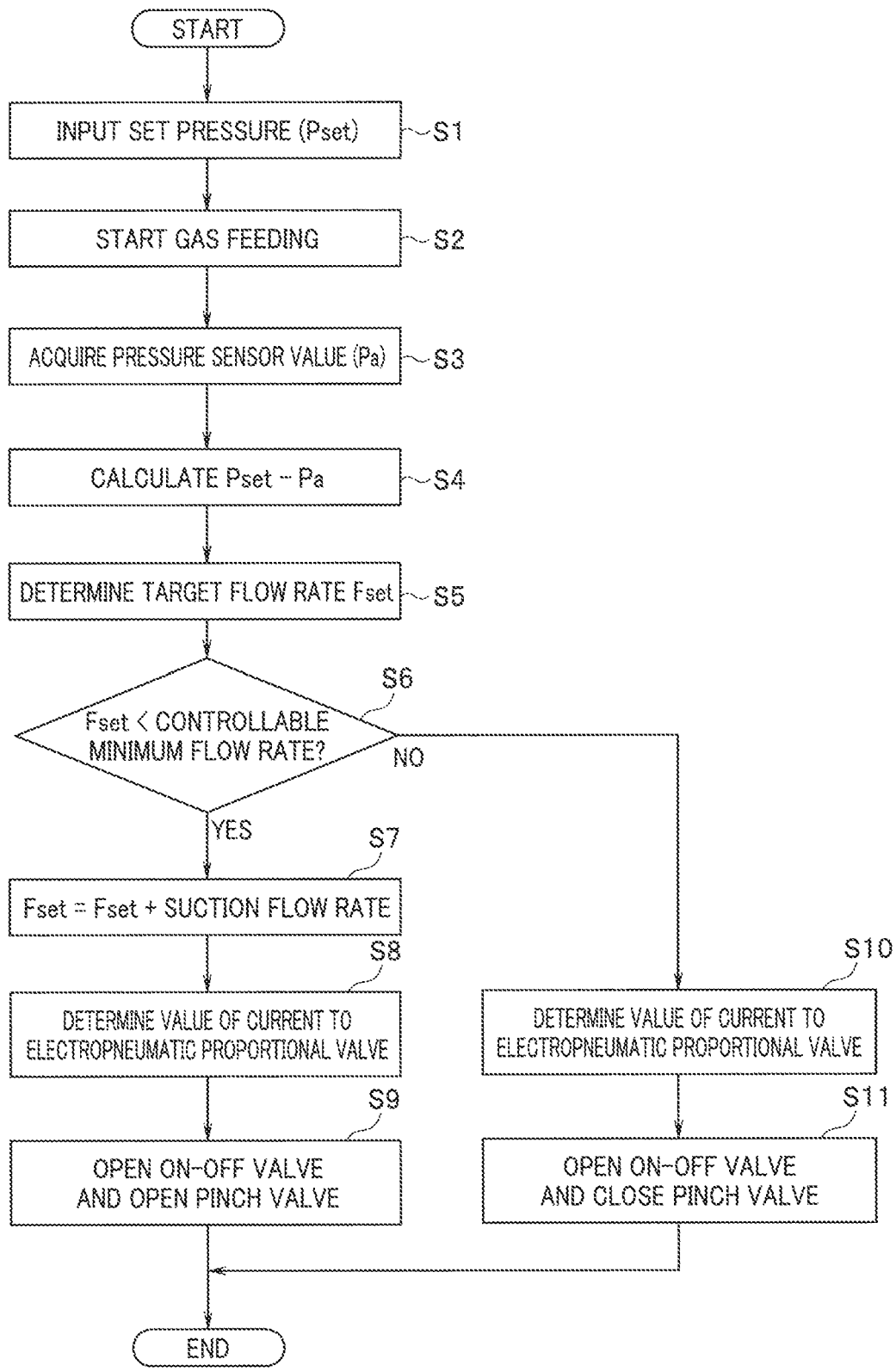
FIG. 2 is a flowchart for description of an exemplary procedure of gas feeding control by the insufflation system.

Subsequently, the procedure of gas feeding control in the insufflation system according to the present embodiment will be described below. FIG. 2 is a flowchart for description of an exemplary procedure of gas feeding control by the insufflation system.

First, an operator or the like inputs set pressure (target pressure) $P_{set}$ of the abdominal cavity 13 as an insufflation target through the setting-display unit 7 (S1). The set pressure $P_{set}$ is outputted to the control unit 6. Subsequently, the insufflation device 1 is driven to start gas feeding from the gas supply source 11 (S2). The gas feeding is performed by intermittent feeding.

Subsequently, abdominal cavity pressure is measured by the pressure sensor 9 at a timing of gas feeding stop (S3). A pressure sensor value $P_a$ as a result of the measurement is outputted to the control unit 6. The control unit 6 calculates a difference between the set pressure $P_{set}$ (insufflation target pressure) of the abdominal cavity and the pressure sensor value $P_a$ (body cavity internal pressure) as the current abdominal cavity pressure (S4). The control unit 6 determines, based on a result of the calculation at S4, a target flow rate $F_{set}$ (first target gas feeding flow rate) at which gas is to be fed into the abdominal cavity (S5).

The control unit 6 determines whether the target flow rate $F_{set}$ is lower than the lowest flow rate $F_{min}$ (threshold gas feeding flow rate) to which control is possible only by the electropneumatic proportional valve 3 (S6). When the target flow rate $F_{set}$ is equal to or higher than the lowest flow rate $F_{min}$ (No at S6), in other words, when the target flow rate $F_{set}$ is in a range in which reliable flow rate adjustment can be performed by the electropneumatic proportional valve 3, the control unit 6 determines the value of current to be applied to the electropneumatic proportional valve 3 to achieve the target flow rate $F_{set}$ and outputs the value of current to the electropneumatic proportional valve 3 (S10). Then, the control unit 6 performs control to open the on-off valve 4 and close the pinch valve 21 (S11) and ends this series of procedures of gas feeding control.

When the target flow rate $F_{set}$ is lower than the lowest flow rate $F_{min}$ (Yes at S6), in other words, when the target flow rate $F_{set}$ is in a range in which reliable flow rate adjustment is difficult to be performed by the electropneumatic proportional valve 3, the control unit 6 resets the target flow rate $F_{set}$ by adding the suction flow rate $F_{asp}$ at the suction device 22 to the target flow rate $F_{set}$ (S7). For example, when the target flow rate $F_{set}$ is 3 L/min and the suction flow rate $F_{asp}$ is 12 L/min, the target flow rate $F_{set}$ (second target gas feeding flow rate) is reset to 15 L/min at S7. In other words, at S7, the suction flow rate $F_{asp}$ is added to the target flow rate $F_{set}$, thereby changing the target flow rate $F_{set}$ to the range in which reliable flow rate adjustment can be performed by the electropneumatic proportional valve 3.

Subsequently, the control unit 6 determines the value of current to be applied to the electropneumatic proportional valve 3 to achieve the target flow rate $F_{set}$ reset at S7 and outputs the value of current to the electropneumatic proportional valve 3 (S8). Then, the control unit 6 performs control to open the on-off valve 4 and open the pinch valve 21 (S9) and ends this series of procedures of gas feeding control.

In this manner, according to the above-described embodiment, the target flow rate $F_{set}$ and the lowest flow rate $F_{min}$ to which control is possible by the electropneumatic proportional valve 3 are compared when gas is to be fed from the insufflation device 1 to an expansion target cavity. When the target flow rate $F_{set}$ is lower than the lowest flow rate $F_{min}$, the pinch valve 21 is opened, gas feeding is performed while gas is suctioned from the expansion target cavity at a predetermined flow rate (the suction flow rate $F_{asp}$) by the suction device 22. Since the gas feeding and suction are both performed, the target flow rate $F_{set}$ of gas feeding from the insufflation device 1 increases by the suction flow rate $F_{asp}$ so that the target flow rate $F_{set}$ is higher than the lowest flow rate $F_{min}$. Thus, a minute flow rate can be stably controlled.

In addition, in the above-described embodiment, flow rate control when the target flow rate $F_{set}$ is lower than the lowest flow rate $F_{min}$ is performed by controlling whether to perform suction by the suction device 22 in accordance with the target flow rate $F_{set}$, and no new component such as a valve or a conduit needs to be provided to a conventional insufflation system. Thus, a minute flow rate can be stably controlled with an inexpensive configuration.

The above-described values of the lowest flow rate $F_{min}$ and the suction flow rate $F_{asp}$ are exemplary and the present invention is not limited to the above-described values. In particular, the value of the flow rate $F_{min}$ as a reference for determination of whether to drive the suction device 22 does not need to be a value equal to 10% of the maximum flow rate but may be, for example, a value in a flow rate range to which control is reliably possible by the electropneumatic proportional valve 3, such as the value of 20% approximately. Moreover, the configuration of the insufflation device 1 illustrated in FIG. 1 is merely exemplary. For example, the configuration in the above description includes one pressure sensor 9 configured to measure the body cavity pressure but may include two kinds of pressure sensors for high pressure measurement and low pressure measurement.

Second Embodiment

In the above-described first embodiment, the suction device 22 suctions gas from the body cavity while the electropneumatic proportional valve 3 controls the flow rate of gas feeding from the insufflation device 1, thereby performing stable control even when the gas feeding flow rate is minute. Difference of the present embodiment is that a proportional control valve 4' (third on-off valve) is provided in the insufflation device 1 and an aperture 24 is provided between the suction device 22 and the pinch valve 21. Specifically, the difference is that the flow rate of gas feeding from the insufflation device 1 is controlled by the electropneumatic proportional valve 3 and the proportional control valve 4' and the flow rate of suction to the suction device 22 is lowered by using the aperture 24.

Figure 3:
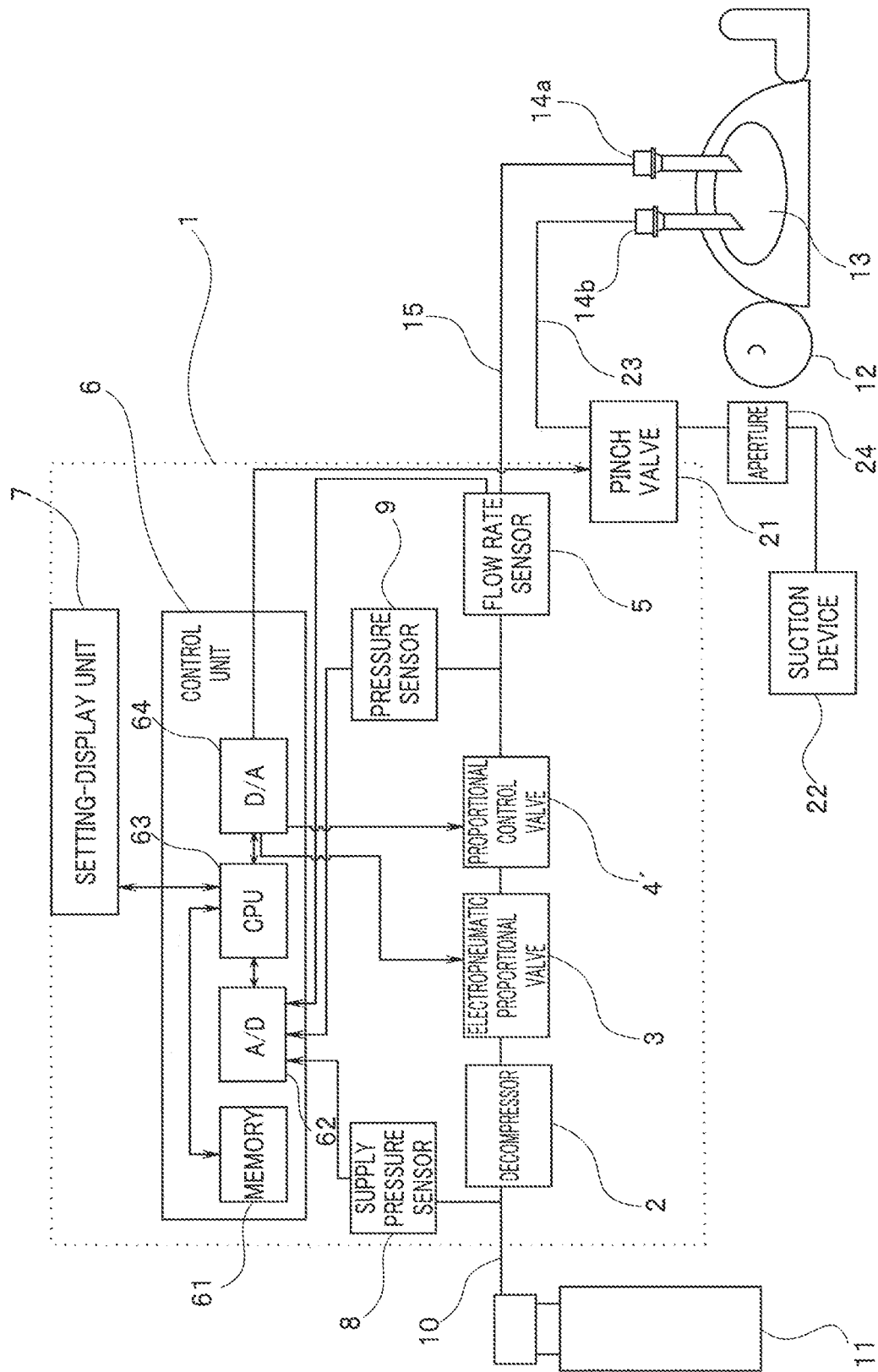
FIG. 3 is a diagram illustrating an exemplary entire configuration of an insufflation system according to a second embodiment.

FIG. 3 is a diagram illustrating an exemplary entire configuration of an insufflation system according to the second embodiment. The insufflation system according to the present embodiment has a configuration same as that of the insufflation system illustrated in FIG. 1 except that the proportional control valve 4' is disposed in place of the on-off valve 4 in the insufflation device 1 and the aperture 24 is provided between the pinch valve 21 and the suction device 22.

The proportional control valve 4' is a kind of electromagnetically driven valve and is an adjustment valve including an electromagnetic coil in a drive unit. When current flows through the electromagnetic coil, magnetic force is generated and suctions a plunger to open and close the valve. The opening degree of a valve part can be controlled by controlling the position of the plunger through the magnitude of current flowing through the electromagnetic coil so that the flow rate of gas flowing through the gas feeding conduit is adjusted to a predetermined value.

The aperture 24 is a site provided to reduce the opening area of a flow path of the suction tube 23 by a predetermined amount. Since the aperture 24 is disposed, the flow rate of suction from the abdominal cavity 13 is lowered by a predetermined amount.

Any component same as that of the insufflation system illustrated in FIG. 1 among other sites included in the insufflation system illustrated in FIG. 3 is denoted by the same reference sign and description of the component is omitted.

Figure 4:
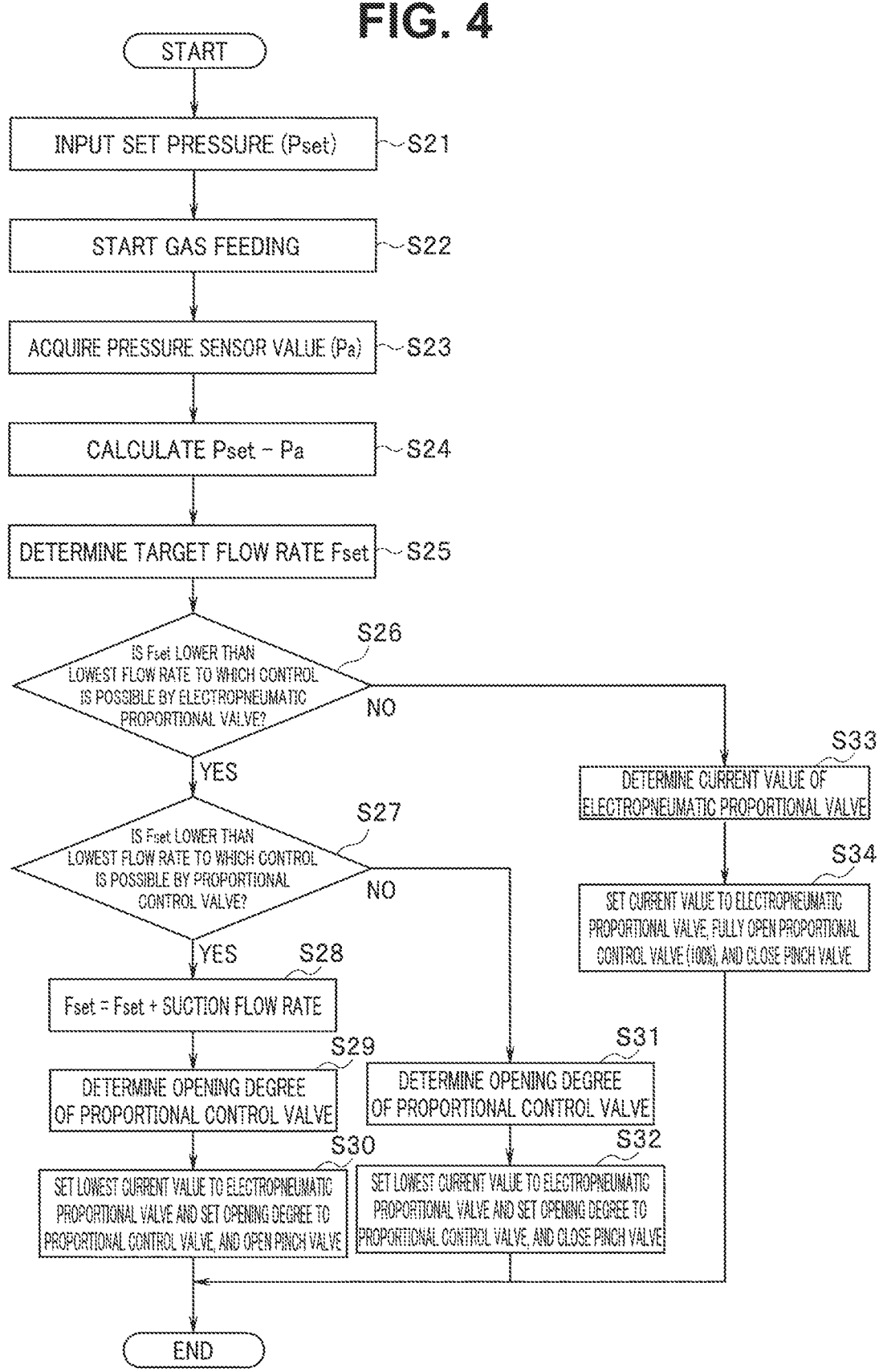
FIG. 4 is a flowchart for description of an exemplary procedure of gas feeding control by the insufflation system according to the second embodiment.

Subsequently, the procedure of gas feeding control in the insufflation system according to the present embodiment will be described below. FIG. 4 is a flowchart for description of an exemplary procedure of gas feeding control by the insufflation system according to the second embodiment.

First, the series of procedures of S21 to S25 are executed to determine the target flow rate $F_{set}$. The procedures of S21 to S25 are same as the procedures of S1 to S5 illustrated in FIG. 2, and thus description of individual steps is omitted. Subsequently, the control unit 6 determines whether the target flow rate $F_{set}$ is lower than a lowest flow rate $F_{e\_min}$ to which control is possible by the electropneumatic proportional valve 3 (S26).

When the target flow rate $F_{set}$ is equal to or higher than the lowest flow rate $F_{e\_min}$ (No at S26), in other words, when the target flow rate $F_{set}$ is in a range in which reliable flow rate adjustment can be performed by the electropneumatic proportional valve 3, the control unit 6 determines the value of current to be applied to the electropneumatic proportional valve 3 to achieve the target flow rate $F_{set}$ and outputs the value of current to the electropneumatic proportional valve 3 (S33). Then, the control unit 6 performs control to fully open the proportional control valve 4' and close the pinch valve 21 (S34) and ends this series of procedures of gas feeding control.

When the target flow rate $F_{set}$ is lower than the lowest flow rate $F_{e\_min}$ (Yes at S26), in other words, when the target flow rate $F_{set}$ is in the range in which reliable flow rate adjustment is difficult to be performed by the electropneumatic proportional valve 3, the control unit 6 determines whether the target flow rate $F_{set}$ is lower than a lowest flow rate $F_{p\_min}$ to which control is possible by the proportional control valve 4' (S27).

When the target flow rate $F_{set}$ is equal to or higher than the lowest flow rate $F_{p\_min}$ (No at S27), in other words, when the target flow rate $F_{set}$ is in a range in which flow rate adjustment can be reliably performed by the proportional control valve 4', the control unit 6 determines the opening degree of the proportional control valve 4' for achieving the target flow rate $F_{set}$, and outputs the opening degree to the proportional control valve 4' (S31). Then, the control unit 6 controls the value of current through the electropneumatic proportional valve 3 to a current value for achieving a rate lower than the lowest flow rate $F_{e\_min}$ and performs control to close the pinch valve 21 (S32), and ends this series of procedures of gas feeding control.

When the target flow rate $F_{set}$ is lower than the lowest flow rate $F_{p\_min}$ (Yes at S27), in other words, when the target flow rate $F_{set}$ is in a range in which reliable flow rate adjustment is difficult to be performed by the proportional control valve 4', the control unit 6 resets the target flow rate $F_{set}$ by adding a suction flow rate $F_{t\_asp}$ of the suction device 22 to the target flow rate $F_{set}$ (S28). For example, when the target flow rate $F_{set}$ is 1 L/min and the suction flow rate $F_{t\_asp}$ is 4 L/min, the target flow rate $F_{set}$ reset at S28 is 5 L/min. When the lowest flow rate $F_{e\_min}$ to which control is possible by the electropneumatic proportional valve 3 is 10 L/min and the opening degree of the proportional control valve 4' at which reliable flow rate adjustment is possible is 20%, the lowest flow rate $F_{p\_min}$ is 2 L/min. In other words, at S28, the target flow rate $F_{set}$ is increased from 1 L/min to 5 L/min by adding the suction flow rate $F_{t\_asp}$ to the target flow rate $F_{set}$ and is changed to the range in which flow rate adjustment can be reliably performed by the proportional control valve 4'.

Subsequently, the control unit 6 determines the opening degree of the proportional control valve 4' for achieving the target flow rate $F_{set}$ reset at S28 and outputs the opening degree to the proportional control valve 4' (S29). Then, the control unit 6 controls the value of current through the electropneumatic proportional valve 3 to a current value for achieving a rate lower than the lowest flow rate $F_{e\_min}$ and performs control to open the pinch valve 21 (S30), and ends this series of procedures of gas feeding control.

In this manner, a threshold value to which the gas feeding flow rate is adjustable by the insufflation device 1 is lowered by adjusting the amount of gas feeding by using the proportional control valve 4' as well as the electropneumatic proportional valve 3. In addition, the aperture 24 is provided on the suction tube 23 to lower the suction flow rate. Thus, the amount of gas discharged from the abdominal cavity 13 can be reduced while a minute flow rate is stably controlled, and thus the amount of gas used for insufflation can be reduced for cost reduction.

Third Embodiment

In the above-described first and second embodiments, the pressure sensor 9 is connected with the gas feeding conduit. Thus, gas feeding needs to be stopped each time the internal pressure of the abdominal cavity is to be measured. Difference of the present embodiment is that the internal pressure of the abdominal cavity is measured during gas feeding by inserting a trocar 14c for pressure measurement into the abdominal cavity 13 so that the internal pressure of the abdominal cavity can be directly measured by a pressure sensor 9' through the trocar 14c.

Figure 5:
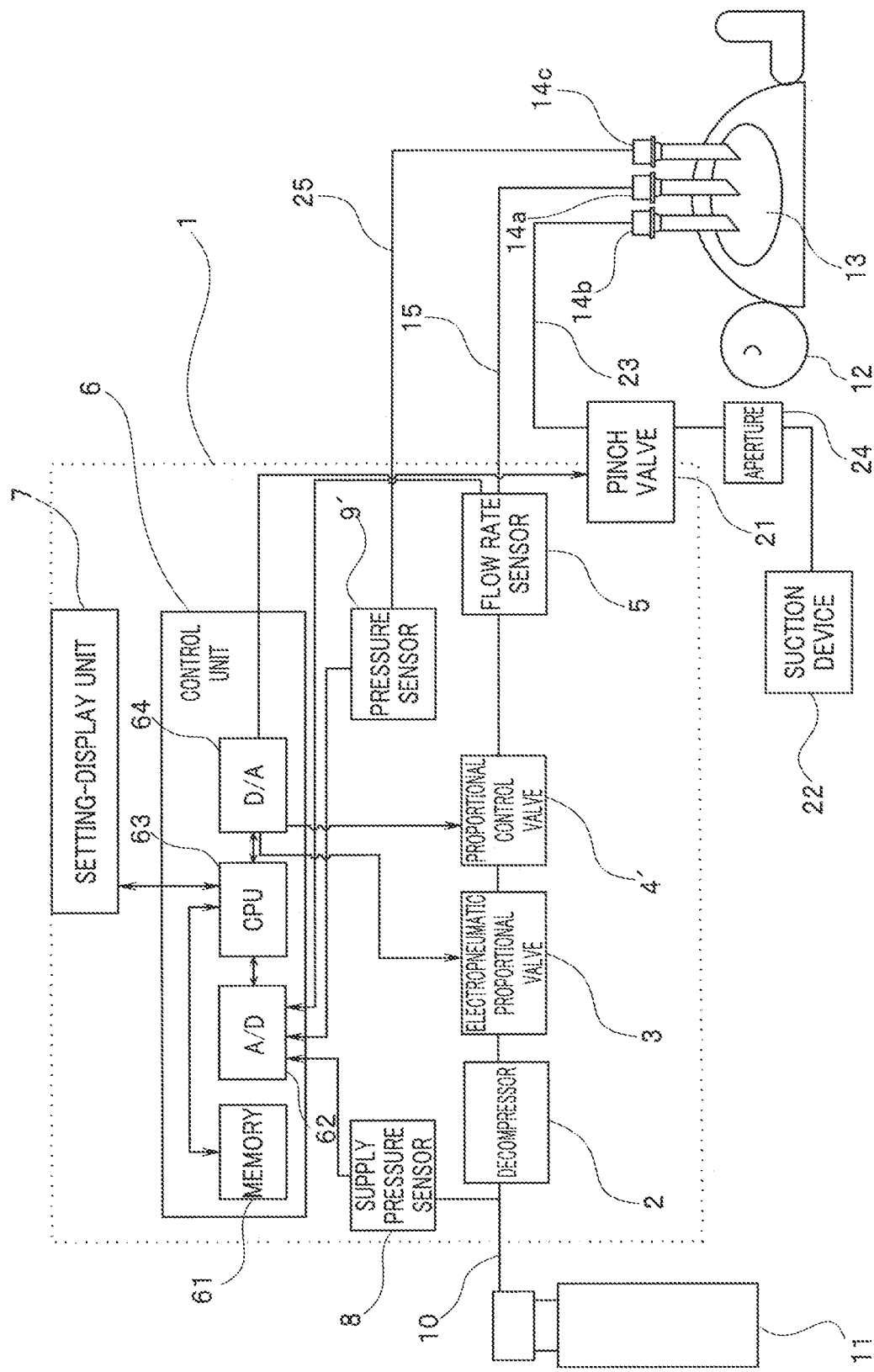
FIG. 5 is a diagram illustrating an exemplary entire configuration of an insufflation system according to a third embodiment.

FIG. 5 is a diagram illustrating an exemplary entire configuration of an insufflation system according to the third embodiment. The insufflation device 1 is connected with a pressure measurement tube 25 (pressure measurement conduit) as well as the gas feeding tube 15. The pressure sensor 9' is connected with the pressure measurement tube 25 to measure the internal pressure of the abdominal cavity through the trocar 14c inserted into the abdominal cavity 13 of the patient 12. The pressure measurement is performed in parallel with gas feeding without stopping the gas feeding.

Any component same as that of the insufflation systems illustrated in FIGS. 1 and 3 among other sites included in the insufflation system illustrated in FIG. 5 is denoted by the same reference sign and description of the component is omitted. The procedure of gas feeding control in the insufflation system according to the present embodiment is same as that in the second embodiment illustrated in FIG. 4.

To control a minute flow rate in a case in which gas is fed into a cavity having a small volume, such as a case in which a rectum is swelled in TaTME (transanal total mesorectal excision), insufflation needs to be performed while gas is continuously suctioned from the cavity by the suction device 22. However, when gas feeding is intermittently performed for pressure measurement, pressure change in the cavity between a gas feeding duration and a gas feeding stop duration is large, which degrades cavity pressure maintaining performance. According to the insufflation system according to the present embodiment, the internal pressure of the cavity can be measured by using the pressure measurement tube 25 connected with the cavity, and thus continuous gas feeding can be performed. Thus, pressure change in the cavity can be prevented while a minute flow rate is stably controlled.

Fourth Embodiment

In the insufflation systems according to the above-described first to third embodiments, the suction device 22 is used to suction and discharge a predetermined amount of gas from the body cavity during gas feeding. Normally, the suction device 22 is also used to discharge smoke generated, for example, when an affected part is cauterized by an electrocautery scalpel or the like in a procedure.

Conventionally, a smoke discharging function of the suction device 22 has been activated when a foot switch (not illustrated) is pressed down by an operator or when use of an electrocautery scalpel is sensed. Stopping of the smoke discharging function has been set by the setting-display unit 7 of the insufflation device 1 or the like when the smoke discharging function is not used in a procedure. In this case, the smoke discharging function is not activated when the foot switch is pressed down nor when an electrocautery scalpel is used. However, the smoke discharging function needs to be activated when the foot switch is pressed down at an optional timing, depending on a procedure or an operator, although a smoke discharging activation function (hereinafter referred to as a smoke discharging cooperative function) that cooperates with use of an electrocautery scalpel is unnecessary. Thus, the present embodiment provides an insufflation system that can stop only the smoke discharging cooperative function when the smoke discharging function is used.

Figure 6:
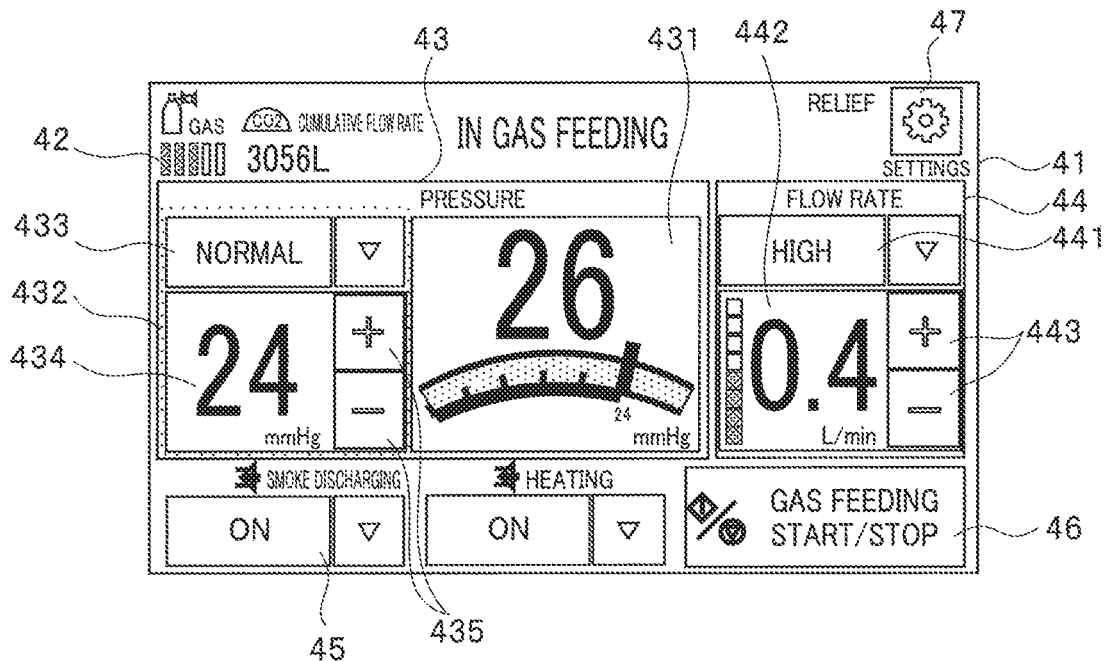
FIG. 6 is a diagram illustrating an exemplary display screen on a setting-display unit 7 in normal operation.

The insufflation system according to the present embodiment has a configuration same as that of the insufflation system illustrated in FIG. 1. Stopping of the smoke discharging cooperative function is performed through a setting screen on the setting-display unit 7. FIG. 6 illustrates an exemplary display screen on the setting-display unit 7 in normal operation.

As illustrated in FIG. 6, a normal operation display screen 41 includes display regions of a supply pressure display region 42, an intraluminal pressure display region 43, and a flow rate display region 44.

In the supply pressure display region 42 provided at an upper-left part of the screen, a pressure value (supply pressure) measured by the supply pressure sensor 8 is displayed, for example, in the format of a level meter. The display format is not limited to the level meter but, for example, the measured value may be displayed intact as a value.

An intraluminal pressure display part 431 and an intraluminal pressure setting part 432 are disposed in the intraluminal pressure display region 43. In the intraluminal pressure display part 431, a pressure value (intraluminal pressure) measured by the pressure sensor 9 is displayed as a value and also displayed in an analog meter format.

A combo box 433 in which an intraluminal pressure mode is set, an intraluminal pressure set value display part 434, and an intraluminal pressure setting button 435 are disposed in the intraluminal pressure setting part 432. The intraluminal pressure mode is a mode set in advance in accordance with the volume of an insufflation target cavity, an operative method, or the like, and for example, three modes, namely, a standard mode, a low-pressure mode, and a high-pressure mode are prepared for the intraluminal pressure mode. An intraluminal pressure set value corresponding to each mode is registered in the memory 61, and when the combo box is operated to change the intraluminal pressure mode, a registered intraluminal pressure set value is read from the memory 61 in association with the changed intraluminal pressure mode and displayed at the intraluminal pressure set value display part 434.

The intraluminal pressure setting button 435 is used to specify a numerical value for the intraluminal pressure set value. The intraluminal pressure set value is increased when "+" of the intraluminal pressure setting button 435 is pressed down, and the intraluminal pressure set value is decreased when "−" of the intraluminal pressure setting button 435 is pressed down. A pressure value set by using the combo box 433 or the intraluminal pressure setting button 435 is displayed at the intraluminal pressure set value display part 434.

A combo box 441 in which a flow rate mode is set, a flow rate display part 442, and a flow rate setting button 443 are disposed in the flow rate display region 44. The flow rate mode is a mode set in advance in accordance with the volume of an insufflation target cavity, an operative method, or the like, and for example, three modes, namely, high, intermediate, and low modes are prepared for the flow rate mode. A flow rate set value corresponding to each mode is registered in the memory 61, and when the combo box is operated to change the flow rate mode, a flow rate set value registered in association with the changed flow rate mode is read from the memory 61 and displayed on the flow rate display part 442.

The flow rate setting button 443 is a button used to specify a numerical value for the flow rate set value. The flow rate set value is increased when "+" of the flow rate setting button 443 is pressed down, and the flow rate set value is decreased when "−" of the flow rate setting button 443 is pressed down. In other words, the scale of a level meter of the flow rate display part 442 is changed in accordance with a flow rate set value set by using the combo box 441 or the flow rate setting button 443.

In addition, a smoke discharging button 45 for instructing execution and stop of smoke discharging operation, a gas feeding button 46 for controlling start and stop of gas feeding, and a setting button 47 for invoking a setting screen for performing setting of each unit of the device are provided on the normal operation display screen 41. Moreover, a display unit, a setting button, and the like in accordance with functions of the insufflation device 1 are disposed as appropriate.

Information of arrangement of parts including display regions such as the supply pressure display region 42, the intraluminal pressure display region 43, and the flow rate display region 44 and various buttons such as the gas feeding button 46 (information of a position at which each part is disposed) on the normal operation display screen 41 is set in the memory 61 in advance. When displaying the normal operation display screen 41 on the setting-display unit 7, the CPU 63 disposes parts necessary for the normal operation display screen 41 by using the arrangement information set in the memory 61 and displays the parts on the setting-display unit 7.

Figure 7:
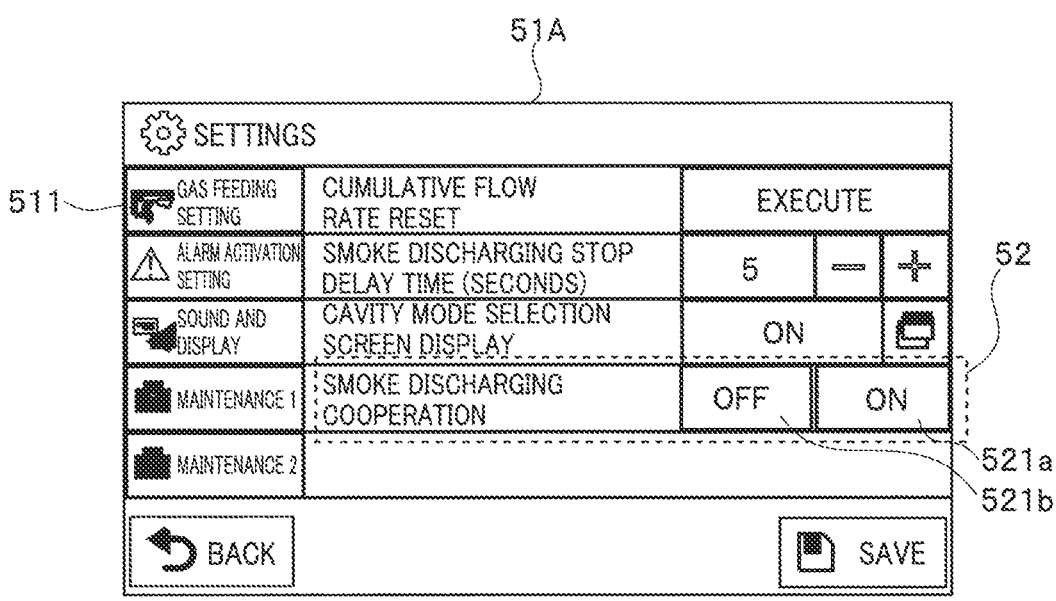
FIG. 7 is a diagram illustrating an exemplary display screen on the setting-display unit 7 in various setting.

FIG. 7 is a diagram illustrating an exemplary display screen on the setting-display unit 7 in various setting. When the setting button 47 of the normal operation display screen 41 is pressed down, various setting screens as illustrated in FIG. 7 are displayed on the setting-display unit 7. FIG. 7 illustrates a detailed setting screen 51A for performing setting related to gas feeding, and the detailed setting screen 51A is displayed by pressing down a gas feeding setting button 511 among various kinds of menu buttons provided on the left side of the screen.

A smoke discharging cooperative function display region 52 is provided on the detailed setting screen 51A. A smoke discharging cooperative function execution button 521a and a smoke discharging cooperative function stop button 521b are disposed in the smoke discharging cooperative function display region 52. When the smoke discharging cooperative function execution button 521a is pressed down, the smoke discharging cooperative function is controlled to an activated state. In other words, the smoke discharging cooperative function is set to a state in which the smoke discharging function is automatically activated upon sensing use of an electrocautery scalpel. When the smoke discharging cooperative function stop button 521b is pressed down, the smoke discharging cooperative function is controlled to a stop state. In other words, while the smoke discharging function is activated, the smoke discharging cooperative function is set to a state in which the smoke discharging function is not activated when use of an electrocautery scalpel is sensed.

In this manner, according to the above-described embodiment, since a setting screen for setting on and off the smoke discharging cooperative function is provided, only the smoke discharging cooperative function can be stopped while the smoke discharging function is activated.

Fifth Embodiment

In a laparoscopic surgical operation in which the insufflation system according to an above-described embodiments is used, mmHg has been conventionally used in Japan as the unit of pressure for the gas feeding pressure, the abdominal cavity pressure, and the like. Along with recent globalization, the system of unit used in medical devices tends to be standardized to the SI units. Accordingly, the unit of pressure used in the insufflation system needs to be switched to hPa.

However, use of conventional mmHg as the unit of pressure is strongly requested depending on a procedure or an operator. Thus, the present embodiment provides an insufflation system that can easily switch the system of unit of displayed pressure.

The insufflation system according to the present embodiment has a configuration same as that of the insufflation system illustrated in FIG. 1. The system of unit of displayed pressure is switched through a setting screen on the setting-display unit 7. A screen on the setting-display unit 7 in normal operation is same as the screen illustrated in FIG. 6. When the setting button 47 of the normal operation display screen 41 is pressed down, various setting screens as illustrated in FIG. 8 are displayed on the setting-display unit 7.

Figure 8:
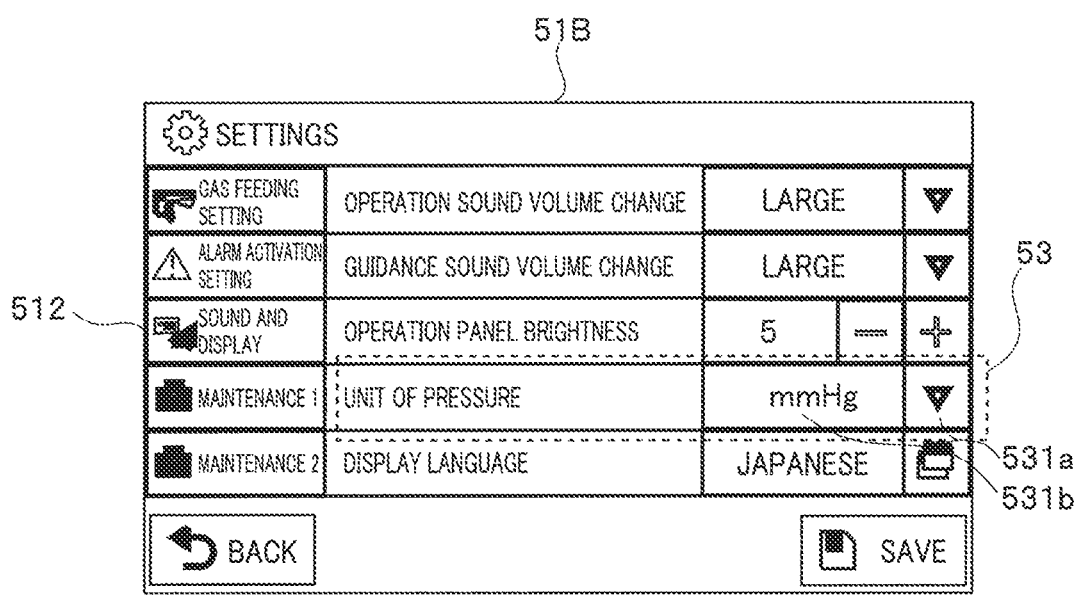
FIG. 8 is a diagram illustrating an exemplary display screen on the setting-display unit 7 in various setting.

FIG. 8 is a diagram illustrating an exemplary display screen on the setting-display unit 7 in various setting. FIG. 8 illustrates a detailed setting screen 51B for performing setting related to sound and display, and the detailed setting screen 51B is displayed by pressing down a sound-display setting button 512 among various kinds of menu buttons provided on the left side of the screen.

A pressure unit setting display region 53 is provided on the detailed setting screen 51B. A combo box 531a for setting the unit of pressure is disposed in the pressure unit setting display region 53. The two units of mmHg and hPa are prepared for the unit of pressure. When the combo box 531a is operated to change the system of unit of displayed pressure, the unit of displayed pressure on all screens displayed on the setting-display unit 7 is switched to a set unit. When the unit switching is performed, a pressure value is calculated in accordance with a predetermined conversion equation by the CPU 63, and a pressure value displayed in each display region is changed (to a value in accordance with the unit of display).

When a pressure value is to be converted by the CPU 63, the pressure value before change is stored in the memory 61. When the unit of display is consecutively switched back to an original unit, the value stored in the memory 61 is read and displayed in the corresponding display region. After unit conversion, an original value cannot be obtained again through consecutive switching, depending on handling of digits after the decimal point in calculation at the CPU 63. However, when a pressure value before change is stored, the original value can be reliably obtained again.

In this manner, according to the above-described embodiment, since a setting screen for switching the system of unit of displayed pressure is provided, the unit of displayed pressure can be easily switched in accordance with needs of a procedure or an operator.

Sixth Embodiment

A conventionally known insufflation system heats gas and feeds the gas into the body cavity. In a known method as a typical method of controlling heating of fed gas, a heater and a temperature sensor are disposed in a gas feeding tube, and at gas feeding, the heater is operated and controlled while the temperature of gas being fed is measured by the temperature sensor, thereby controlling the temperature of gas being fed. However, the gas feeding tube cannot be reused but needs to be discarded at each procedure. The temperature sensor is expensive, and thus use of a conventional heating-type gas feeding tube in which the heater and the temperature sensor are disposed leads to high cost. Thus, the present embodiment provides an insufflation system that can control heating of fed gas at low cost.

Figure 9:
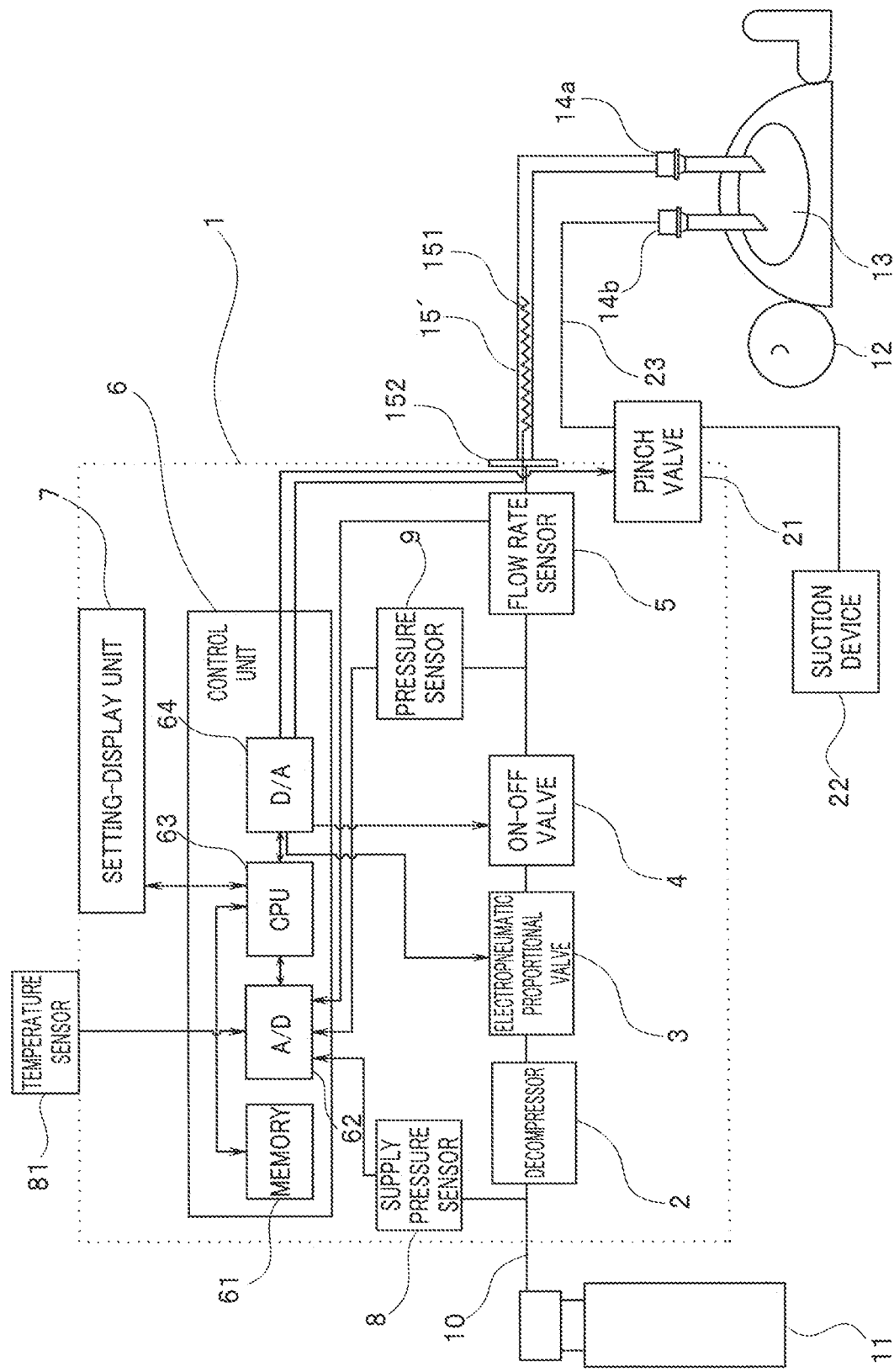
FIG. 9 is a diagram illustrating an exemplary entire configuration of an insufflation system according to a sixth embodiment.

FIG. 9 is a diagram illustrating an exemplary entire configuration of an insufflation system according to the sixth embodiment. As illustrated in FIG. 9, the insufflation system according to the present embodiment includes the insufflation device 1 and the suction device 22. The insufflation device 1 mainly includes the decompressor 2, the electropneumatic proportional valve 3, the on-off valve 4, the flow rate sensor 5, the supply pressure sensor 8, the pressure sensor 9, the control unit 6, the setting-display unit 7, the pinch valve 21, and a temperature sensor 81.

The insufflation device 1 is connected with the gas supply source 11 (for example, a carbon dioxide gas cylinder) through the high-pressure gas tube 10. The insufflation device 1 is also connected with a gas feeding tube 15' as a gas feeding conduit for feeding insufflation gas such as carbon dioxide gas into the abdominal cavity 13 of the patient 12 through the trocar 14a inserted into the body cavity. FIG. 1 illustrates an example in which the abdominal cavity 13 is an insufflation target site, but the insufflation target site may be another site such as the retroperitoneal space, the chest cavity, the subcutaneous space, the rectum, or the large intestine. The trocar 14a is inserted into the insufflation target site.

The decompressor 2 depressurizes high-pressure gas supplied from the gas supply source 11 to pressure that is harmless to the human body. For example, gas supplied from the gas supply source 11 at a high pressure of 6 MPa approximately is depressurized to 50 to 80 mmHg approximately.

The electropneumatic proportional valve 3 is an electrically driven valve and can adjust gas feeding pressure to a predetermined pressure value by changing decompression spring force acting on a valve part to electrically adjust the opening degree of the valve part at multiple stages. The opening degree of the valve is adjusted by adjusting the amount of current applied to the valve based on a control signal inputted from the control unit 6 so that the pressure of carbon dioxide gas depressurized by the decompressor 2 changes to gas feeding pressure in the range of 0 to 80 mmHg approximately.

The on-off valve 4 can feed gas into the gas feeding conduit and stop the feeding by switching opening and closing of a valve part based on a control signal inputted from the control unit 6.

The supply pressure sensor 8 measures pressure in the gas feeding conduit. The pressure measurement is performed at gas supply. The pressure of gas supplied from the gas supply source 11 is measured and a result of the measurement is outputted to the control unit 6.

The pressure sensor 9 measures the pressure of the abdominal cavity 13 through the gas feeding tube 15'. The pressure measurement is performed during gas feeding stopping. A result of the measurement by the pressure sensor 9 is outputted to the control unit 6.

The flow rate sensor 5 measures the flow rate of carbon dioxide gas supplied into the body cavity and outputs a result of the measurement to the control unit 6.

The gas feeding tube 15' is a tube through which gas sent from the insufflation device 1 is guided to the trocar 14a, and has a heating function. Specifically, a heater 151 is provided inside the tube. The gas feeding tube 15' is connected with the gas feeding conduit of the insufflation device 1 through a connector 152. Typically, the tube is formed of flexible material and has a length of 3 m approximately.

The temperature sensor 81 is disposed on one outer surface of the insufflation device 1 and measures the temperature of an atmosphere around the device.

The control unit 6 as a determination unit and a display control unit controls each unit in the insufflation device 1. The control unit 6 mainly includes the memory 61, the analog/digital converter (hereinafter abbreviated as A/D) 62, the CPU 63, and the digital/analog converter (hereinafter abbreviated as D/A) 64.

The memory 61 stores, for example, various set values such as supply pressure, intraluminal pressure, and flow rate, the lowest flow rate $F_{min}$ to which control is possible by the electropneumatic proportional valve 3, and the suction flow rate $F_{asp}$ of the suction device 22. Normally, the lowest flow rate $F_{min}$ to which control is possible by the electropneumatic proportional valve 3 is a value equal to 10% approximately of the maximum flow rate. For example, the lowest flow rate $F_{min}$ is 5 L/min when the maximum flow rate is 50 L/min. In addition, the memory 61 stores various kinds of information related to screens, such as screen patterns to be displayed on the setting-display unit 7 and display patterns of warning messages.

The A/D 62 reads data (analog value) measured by each of the supply pressure sensor 8, the pressure sensor 9, the flow rate sensor 5, and the temperature sensor 81, converts the data into a digital value, and outputs the digital value to the CPU 63.

The CPU 63 reads various set values stored in the memory 61 and collates the set values to measurement data inputted from the A/D 62. The opening degree of the electropneumatic proportional valve 3 and opening and closing of the pinch valve 21 are set based on a result of the collation so that the supply pressure and the flow rate have optimum values. In addition, the value of voltage applied to the heater 151 and needed to output gas having a target temperature is calculated from the temperature inputted from the temperature sensor 81. The set value is outputted to the D/A 64.

The D/A 64 controls the opening degree of the electropneumatic proportional valve 3 and opening and closing of the pinch valve 21 in accordance with the set values inputted from the CPU 63. The D/A 64 also controls voltage applied to the heater 151 disposed in the gas feeding tube 15'.

The setting-display unit 7 is provided on the front panel of the insufflation device 1 and displays an appropriate screen in accordance with an instruction from the CPU 63. Normally, the front panel can receive inputting from a user by a touch panel scheme. Contents inputted from the user such as various set values are outputted from the setting-display unit 7 to the CPU 63. The CPU 63 changes, in accordance with the inputted contents, a screen to be displayed by the setting-display unit 7 and various set values stored in the memory 61.

The suction device 22 is connected with the suction tube 23 as a suction conduit for suctioning gas that fills the body cavity through the trocar 14b inserted into the abdominal cavity 13 of the patient 12. The pinch valve 21 is installed halfway through the suction tube 23. In the present embodiment, the suction device 22 does not have a function to adjust the suction flow rate, and the suction flow rate $F_{asp}$ is a fixed value. For example, the suction flow rate $F_{asp}$ is 12 L/min approximately.

The pinch valve 21 opens and closes a flow path by pinching the suction tube 23. The flow path opening and closing are performed based on a control signal inputted from the control unit 6.

In this manner, according to the above-described embodiment, since control of a heater configured to adjust heating temperature of fed gas is performed based on temperature measured by the temperature sensor 81 provided to the insufflation device 1, no temperature sensor needs to be disposed in the gas feeding tube 15'. Thus, an insufflation system that can control heating of fed gas can be achieved at low cost.

(First Modification)

In the above-described sixth embodiment, one temperature sensor is disposed on one outer surface of the insufflation device 1. Difference of the present modification is that two temperature sensors are disposed on one outer surface of the insufflation device 1.

Figure 10:
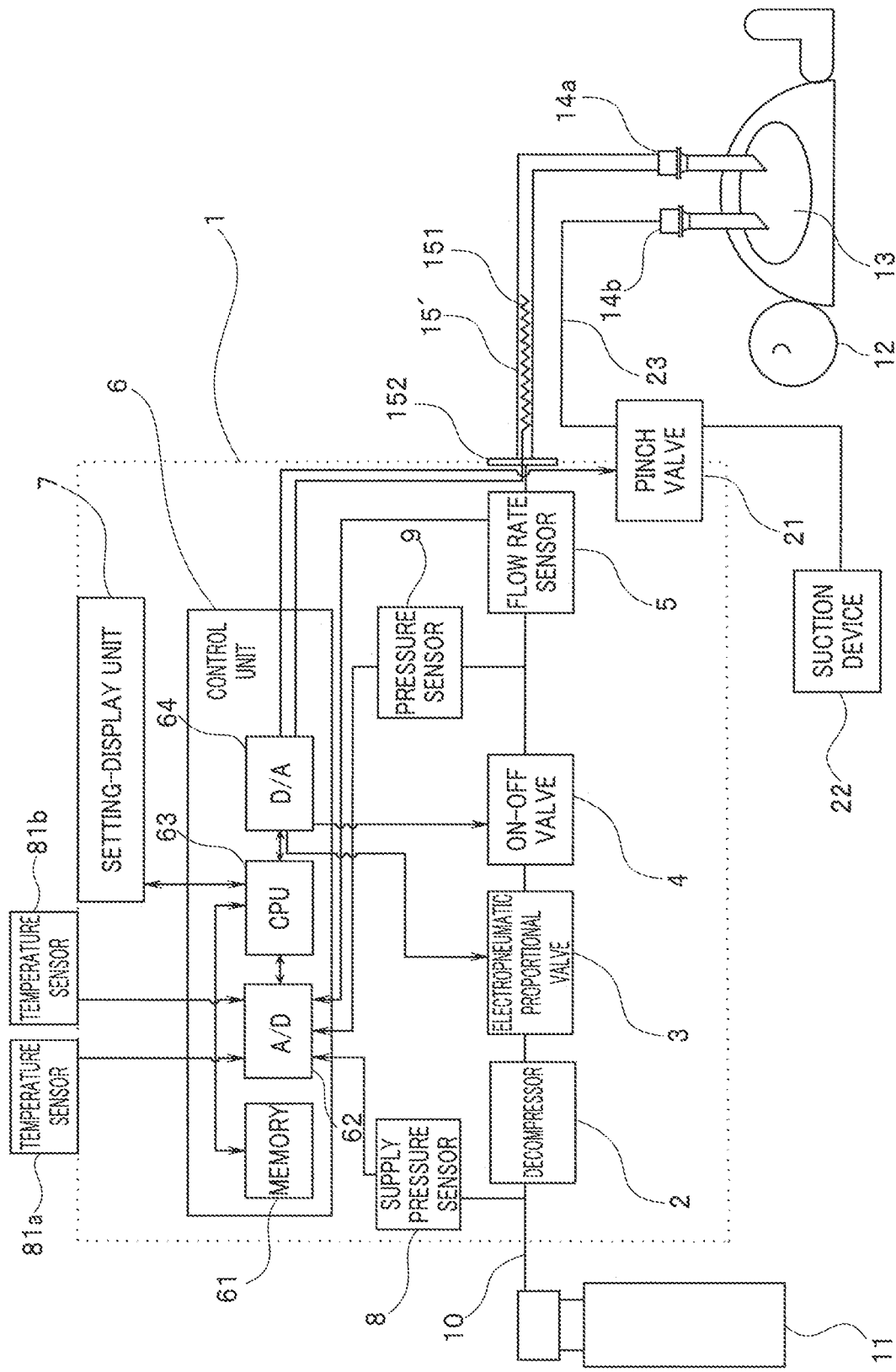
FIG. 10 is a diagram illustrating an exemplary entire configuration of an insufflation system according to a first modification of the sixth embodiment.

FIG. 10 is a diagram illustrating an exemplary entire configuration of an insufflation system according to the first modification of the sixth embodiment. The insufflation system according to the present modification has a configuration same as that of the insufflation system illustrated in FIG. 9 except that two temperature sensors 81a and 81b are disposed adjacent to each other on one outer surface of the insufflation device 1. The temperature sensors 81a and 81b each measure the temperature of an atmosphere around the device. The values measured by the temperature sensors 81a and 81b are inputted to the CPU 63 through the A/D 62.

The CPU 63 calculates difference between the values measured by the temperature sensors 81a and 81b. When the calculated difference exceeds a threshold value (for example, 3.0° C.) stored in the memory 61 in advance, it is determined that at least one of the temperature sensors 81a and 81b has failed. When the failure is determined, control is performed to stop voltage application to the heater 151. Specifically, the value of voltage applied to the heater 151 is set to 0 V.

When the calculated difference is equal to or smaller than the threshold value (for example, 3.0° C.) stored in the memory 61 in advance, it is determined that the temperature sensors 81a and 81b normally perform temperature measurement. Then, an average value of the measured values is calculated, and the value of voltage applied to the heater 151 and needed to output gas having a target temperature is calculated. The set value is outputted to the D/A 64.

The heater 151 is potentially wrongly controlled when temperature is not correctly detected due to failure of a temperature sensor. Thus, in the present modification, the same temperature (temperature around the insufflation device 1) is measured by two temperature sensors, and failure of any temperature sensor is sensed based on difference in the measured temperature. When failure of any temperature sensor is sensed, gas heating by the heater 151 is not performed but normal gas feeding control is performed, thereby preventing wrong control of the heater 151.

(Second Modification)

In the above-described first modification, the two temperature sensors 81a and 81b are disposed adjacent to each other on one outer surface of the insufflation device 1. Difference of the insufflation system according to the present modification is that the temperature sensors 81a and 81b are disposed on two different outer surfaces, respectively, of the insufflation device 1.

Figure 11:
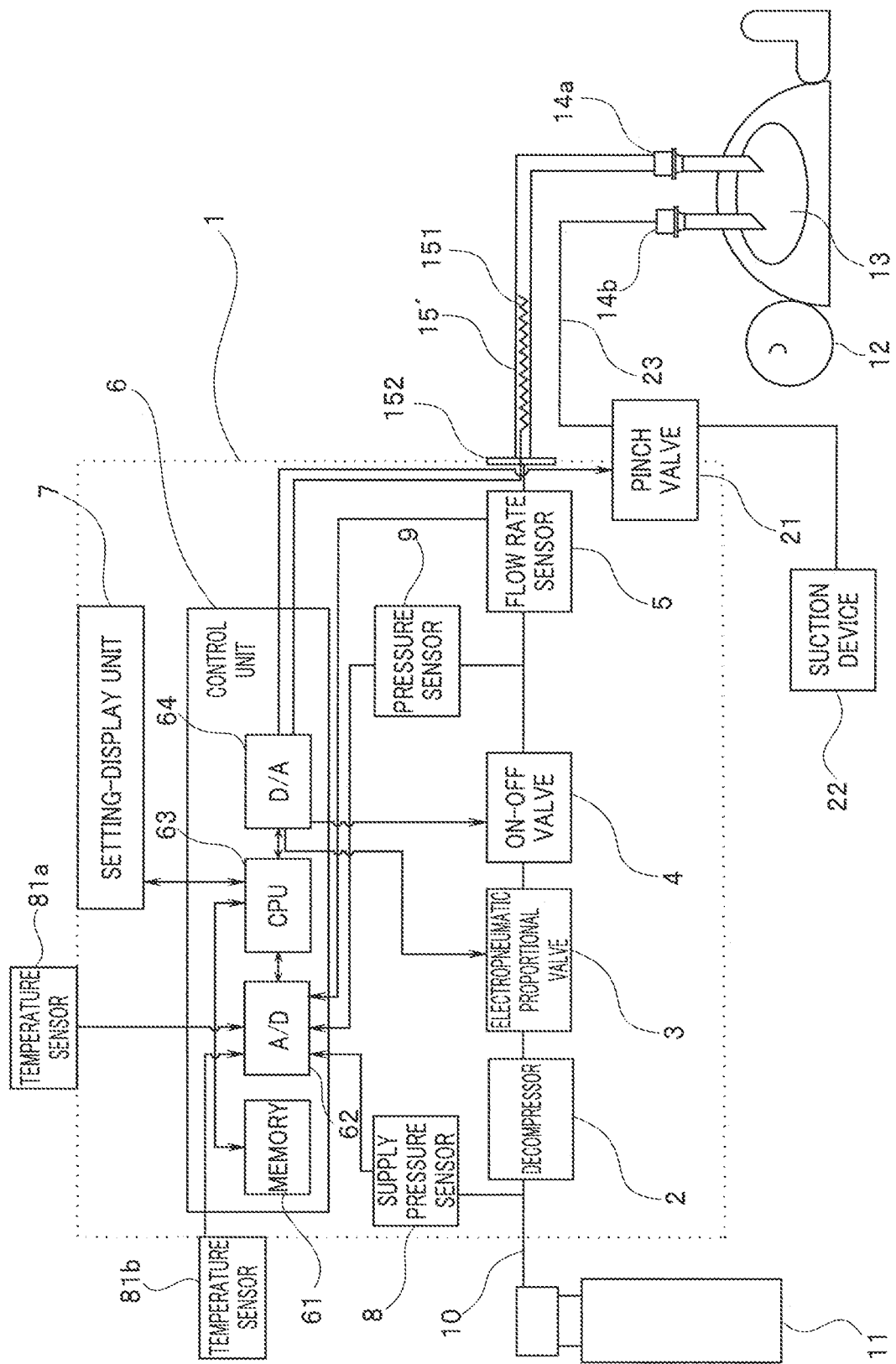
FIG. 11 is a diagram illustrating an exemplary entire configuration of an insufflation system according to a second modification of the sixth embodiment.

FIG. 11 is a diagram illustrating an exemplary entire configuration of an insufflation system according to a second modification of the sixth embodiment. The insufflation system according to the present modification has a configuration same as that of the insufflation system illustrated in FIG. 10 except for disposition of the two temperature sensors 81a and 81b in the insufflation device 1.

The temperature sensors 81a and 81b are disposed on different outer surfaces, respectively, of the insufflation device 1. In the example illustrated in FIG. 11, the temperature sensor 81a is disposed on a surface on which the setting-display unit 7 is installed, and the temperature sensor 81b is disposed on a surface connected with the high-pressure gas tube 10.

Values measured by the temperature sensors 81a and 81b are inputted to the CPU 63 through the A/D 62.

The CPU 63 calculates difference between the values measured by the temperature sensors 81a and 81b. When the calculated difference exceeds a threshold value (for example, 3.0° C.) stored in the memory 61 in advance, it is determined that at least one of the temperature sensors 81a and 81b has failed or disturbance has occurred near a place at which either temperature sensor is disposed. When failure or disturbance occurrence is determined, control is performed to stop voltage application to the heater 151. Specifically, the value of voltage applied to the heater 151 is set to 0 V.

When the calculated difference is equal to or smaller than the threshold value (for example, 3.0° C.) stored in the memory 61 in advance, it is determined that the temperature sensors 81a and 81b normally perform temperature measurement. Then, an average value of the measured values is calculated, and the value of voltage applied to the heater 151 and needed to output gas having a target temperature is calculated. The set value is outputted to the D/A 64.

The heater 151 is potentially wrongly controlled when temperature is not correctly detected due to failure of any temperature sensor or disturbance. Thus, in the present modification, difference between values measured by two temperature sensors is calculated to sense failure of any temperature sensor or disturbance occurrence. When failure of any temperature sensor or disturbance occurrence is sensed, gas heating by the heater 151 is not performed but normal gas feeding control is performed, thereby preventing wrong control of the heater 151.

Figure 12:
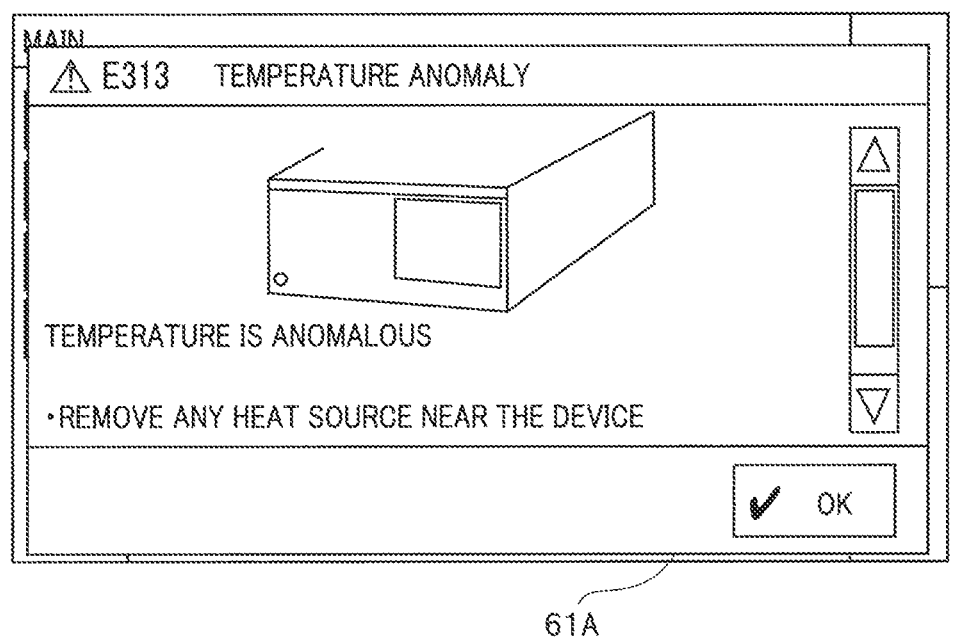
FIG. 12 is a diagram illustrating an exemplary display screen on the setting-display unit 7 in anomaly occurrence.

When the difference between the values measured by the temperature sensors 81a and 81b exceeds the threshold value, the CPU 63 may distinguish failure and disturbance occurrence, and when disturbance occurrence is determined, any factor may be removed to continue gas heating. When the difference between the values measured by the temperature sensors 81a and 81b exceeds the threshold value, the CPU 63 notifies an operator or the like of an anomaly, for example, by causing the setting-display unit 7 to display an alarm screen 61A as illustrated in FIG. 12. FIG. 12 is a diagram illustrating an exemplary display screen on the setting-display unit 7 in anomaly occurrence.

When disturbance that increases the temperature around the insufflation device 1 is found through the alarm screen 61A as illustrated in FIG. 12 and is removed by the operator or the like, the difference between the values measured by the temperature sensors 81a and 81b becomes equal to or smaller than the threshold value. Accordingly, heating of fed gas can be securely continued.

Figure 13:
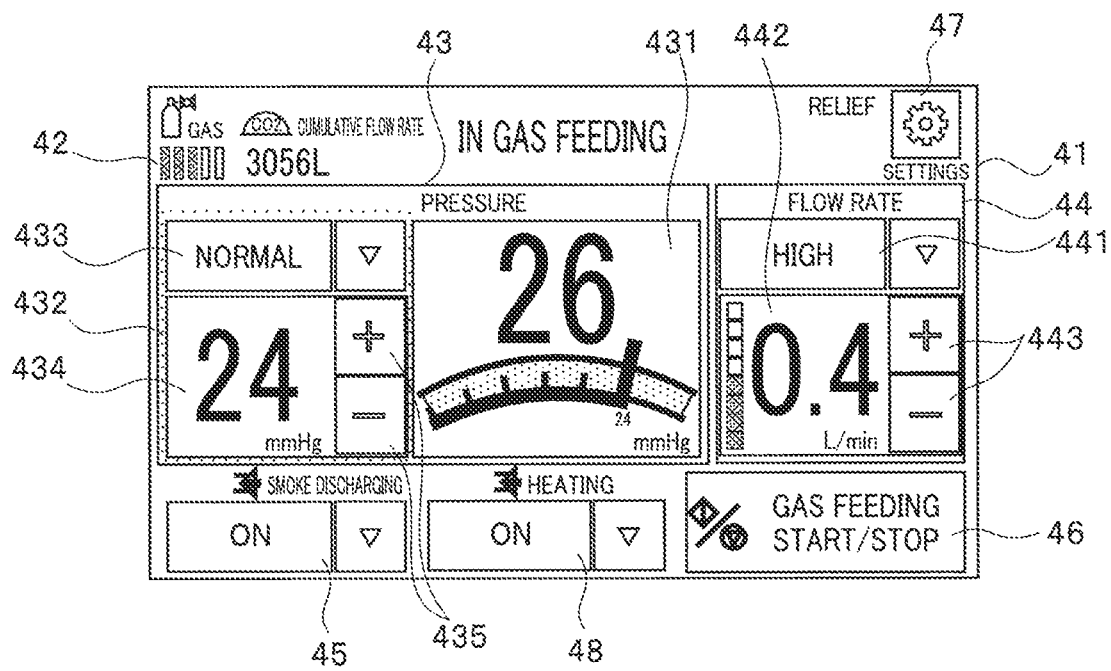
FIG. 13 is a diagram illustrating an exemplary display screen on the setting-display unit 7 in normal operation.

FIG. 13 is a diagram illustrating an exemplary display screen on the setting-display unit 7 in normal operation. In the above description, heating is automatically stopped by the CPU 63 on the device side when an anomaly of measured temperature is sensed, but the operator may desire to stop the heating depending on a situation. Thus, a heating button 48 for instructing execution and stop of heating operation is provided on the normal operation display screen 41 as illustrated in FIG. 13. When the heating button 48 is switched off, a control instruction is inputted to set voltage applied to the heater 151 to 0 V. In this manner, the operator can intentionally stop gas heating in normal heating gas feeding operation.

Figure 14:
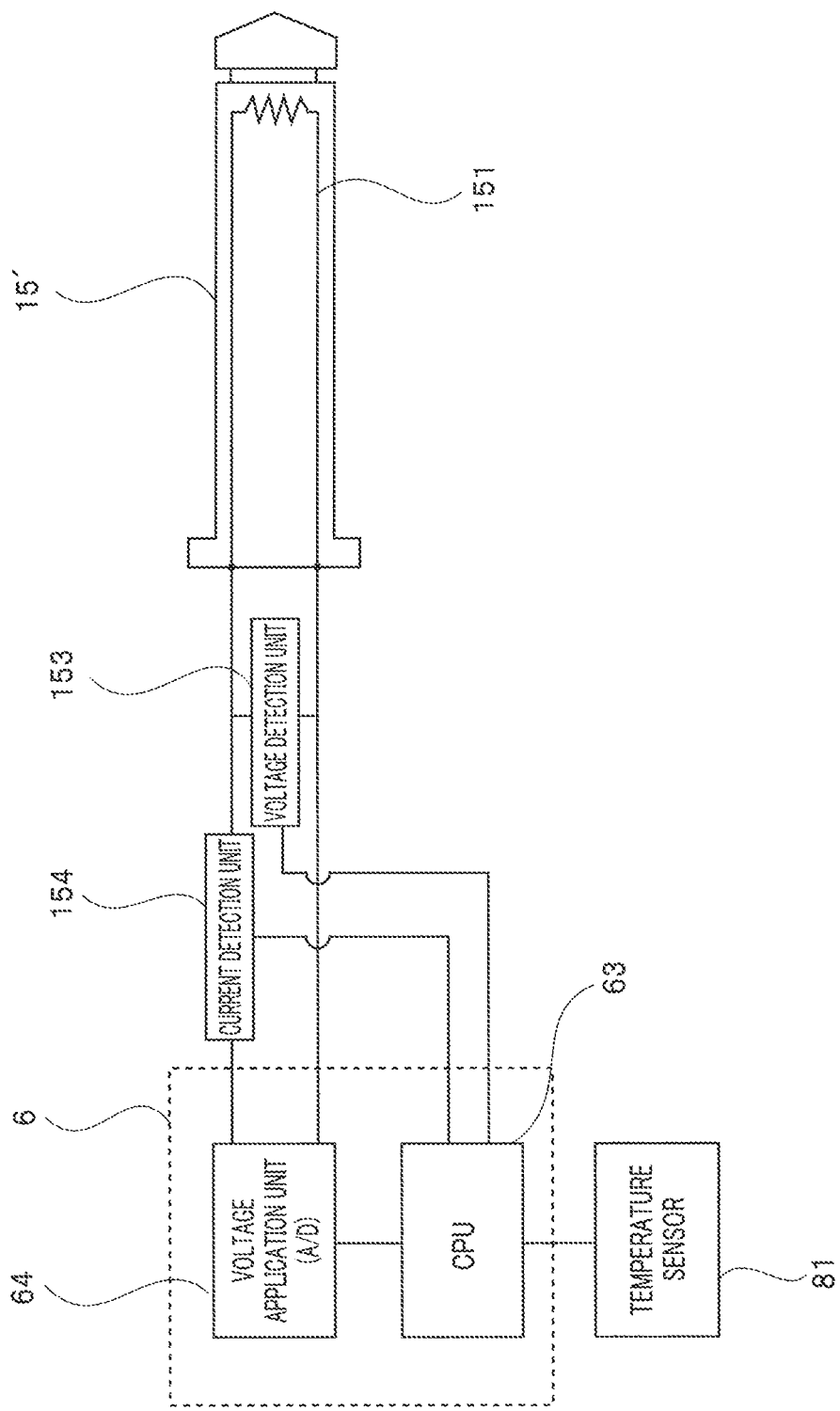
FIG. 14 is a diagram for description of an exemplary configuration of a site that senses connection of a gas feeding tube 15'.

FIG. 14 is a diagram for description of an exemplary configuration of a site that senses connection of the gas feeding tube 15'. Voltage cannot be correctly applied to the heater 151 when the gas feeding tube 15' is not correctly connected with the insufflation device 1 although it is determined that no failure of the temperature sensors 81a and 81b nor disturbance has occurred and heating by the heater 151 is possible. Thus, the state of connection of the gas feeding tube 15' is sensed, and voltage application to the heater 151 is stopped when it is determined that the connection is not correct.

As illustrated in FIG. 14, a voltage detection unit 153 and a current detection unit 154 are provided in the insufflation device 1. The voltage detection unit 153 is connected in parallel with the heater 151, and the current detection unit 154 is connected in series with the heater 151. Values measured by the voltage detection unit 153 and the current detection unit 154 are inputted to the CPU 63 through the A/D 62.

The CPU 63 compares the values measured by the voltage detection unit 153 and the current detection unit 154 with a threshold value stored in the memory 61 in advance, and determines that the gas feeding tube 15' is not correctly connected with the insufflation device 1 when at least one of the measured values is smaller than the threshold value. In this case, control is performed to stop voltage application to the heater 151. Specifically, the value of voltage applied to the heater 151 is set to 0 V.

When the values measured by the voltage detection unit 153 and the current detection unit 154 are equal to or higher than the threshold value stored in the memory 61 in advance, it is determined that the gas feeding tube 15' is correctly connected with the insufflation device 1. In this case, the value of voltage applied to the heater 151 and needed to output gas having a target temperature is calculated. The set value is outputted to the D/A 64.

In this manner, since the situation of connection of the gas feeding tube 15' is monitored, the heater 151 can be prevented from being wrongly controlled when the heater 151 is not correctly connected.

The values measured by the voltage detection unit 153 and the current detection unit 154 may be continuously monitored and compared with target electrical power, thereby controlling application voltage to the heater 151.

Seventh Embodiment

In the above-described sixth embodiment, heating of fed gas is controlled based on the temperature around the insufflation device 1 (atmosphere temperature). Difference of the present embodiment is that a temperature sensor 81c is provided in the insufflation device 1 to directly measure the temperature of fed gas and heating of fed gas is controlled based on the measured temperature.

Figure 15:
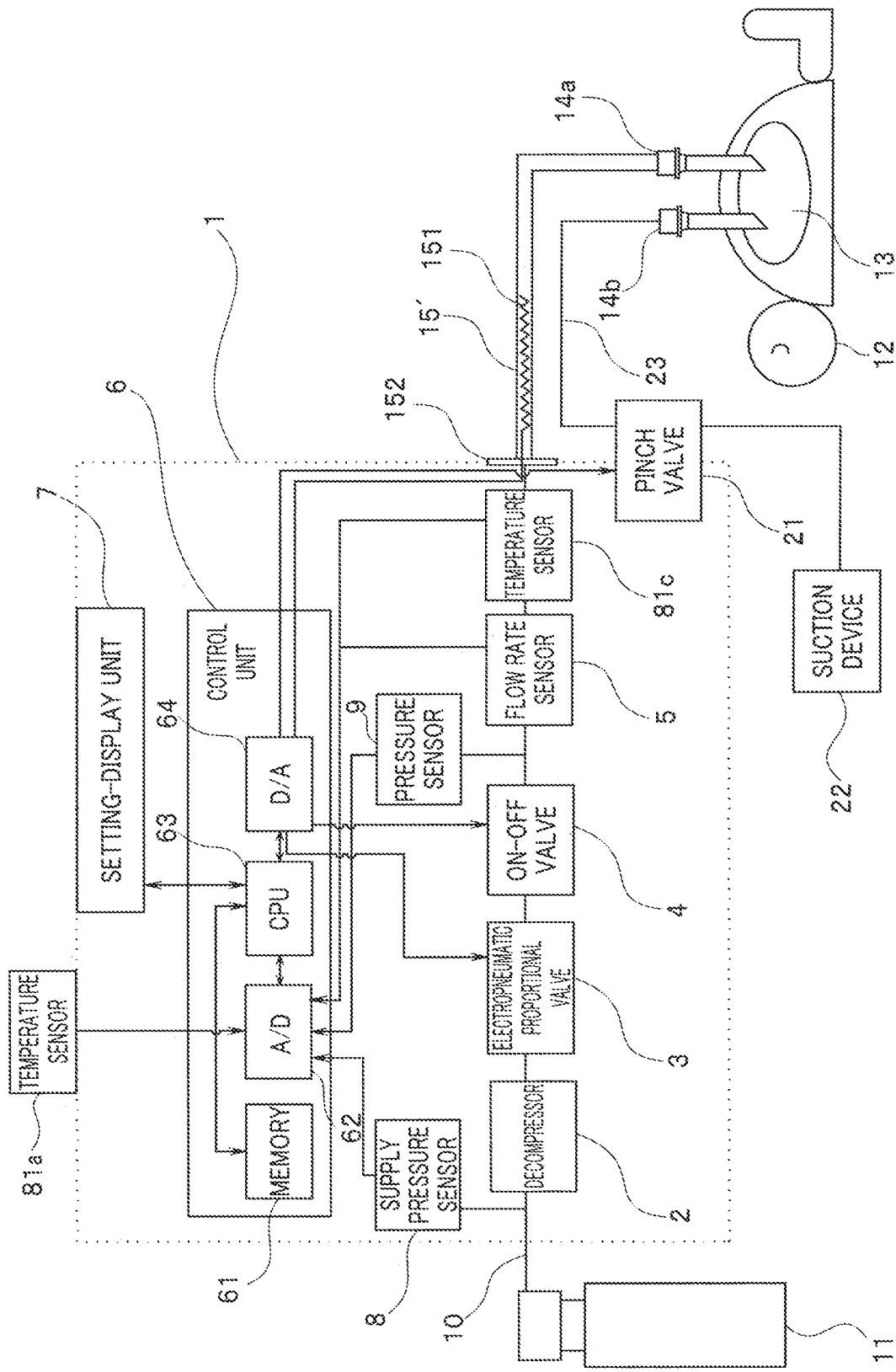
FIG. 15 is a diagram illustrating an exemplary entire configuration of an insufflation system according to a seventh embodiment.

FIG. 15 is a diagram illustrating an exemplary entire configuration of an insufflation system according to the seventh embodiment. The insufflation system according to the present embodiment has a configuration same as that of the insufflation system illustrated in FIG. 9 except that the temperature sensor 81a is disposed on one outer surface of the insufflation device 1 and the temperature sensor 81c is provided inside the insufflation device 1 to measure the temperature of gas in the gas feeding conduit. Values measured by the temperature sensors 81a and 81c are inputted to the CPU 63 through the A/D 62.

Upon activation of the device, the CPU 63 calculates difference between the values measured by the temperature sensors 81a and 81c. When the calculated difference exceeds a threshold value (for example, 3.0° C.) stored in the memory 61 in advance, it is determined that at least one of the temperature sensors 81a and 81c has failed. When the failure is determined, voltage application to the heater 151 is not performed but normal gas feeding control is performed.

When the calculated difference is equal to or smaller than the threshold value (for example, 3.0° C.) stored in the memory 61 in advance, it is determined that the temperature sensors 81a and 81c normally perform temperature measurement. The CPU 63 calculates an average value of the measured values and calculates the value of voltage applied to the heater 151 and needed to output gas having a target temperature. The set value is outputted to the D/A 64, predetermined voltage is applied to the heater 151, and heating is started.

During gas feeding as well, the CPU 63 continuously monitors the value measured by the temperature sensor 81c. When the measured value has decreased, the CPU 63 corrects the value of voltage applied to the heater 151.

Normally, the temperature of gas before heating is equal to the temperature of an atmosphere around the system. However, while continuing gas decompression by the decompressor 2, the decompressor 2 is cooled as time elapses, and accordingly, the temperature of gas outputted from the decompressor 2 becomes lower than the temperature of the atmosphere. In this state, when the gas temperature is approximated by the temperature of the atmosphere and gas heating is controlled, temperature lower than an expected temperature is potentially obtained. Thus, in the present embodiment, the temperature sensor 81c is provided in the insufflation device 1 to measure the actual temperature of the gas, thereby more accurately controlling gas heating.

Gas heating also depends on the flow rate of fed gas. Specifically, as the flow rate of gas feeding is higher, heating efficiency decreases, and thus voltage applied to the heater 151 needs to be higher. For this, during gas feeding, the CPU 63 adjusts an applied voltage value calculated from measured temperature, by using the flow rate of fed gas measured by the flow rate sensor 5, and outputs the applied voltage value to the D/A 64. Accordingly, gas heating can be more accurately controlled.

Eighth Embodiment

It is important that, before use, an insufflation system as a medical device is inspected to check that the device has no anomaly. However, the inspection needs a broad range of operation items and setting options of the insufflation device 1 and takes a reasonable amount of time and work, and thus has been difficult to be easily performed. In addition, in measurement of flow rate accuracy, control of gas feeding by the insufflation device 1 is intermittent, and thus it has been difficult to check the accuracy. For these reasons, the present embodiment provides an insufflation system that can be easily inspected.

The insufflation system according to the present embodiment has a configuration same as that of the insufflation system illustrated in FIG. 9. Various kinds of setting for performing inspection are performed through a setting screen on the setting-display unit 7. A screen on the setting-display unit 7 in normal operation is same as the screen illustrated in FIG. 6. When the setting button 47 of the normal operation display screen 41 is pressed down, various setting screens as illustrated in FIG. 16 are displayed on the setting-display unit 7.

Figure 16:
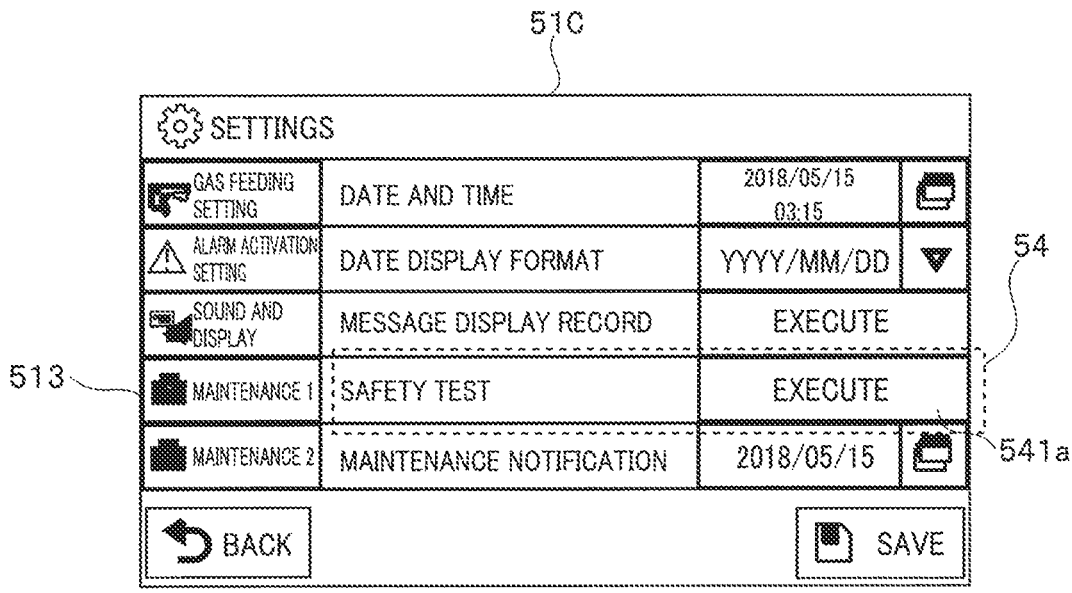
FIG. 16 is a diagram illustrating an exemplary display screen on the setting-display unit 7 in various setting.

FIG. 16 is a diagram illustrating an exemplary display screen on the setting-display unit 7 in various setting. FIG. 16 illustrates a detailed setting screen 51C for performing setting related to inspection, and the detailed setting screen 51C is displayed by pressing down a "maintenance 1" button 513 among various kinds of menu buttons provided on the left side of the screen.

A safety test display region 54 that indicates inspection is provided on the detailed setting screen 51C. An execution button 541*a* is disposed in the safety test display region 54. An inspection screen 54A as illustrated in FIG. 17 is displayed on the setting-display unit 7 by pressing down the execution button 541*a*.

Figure 17:
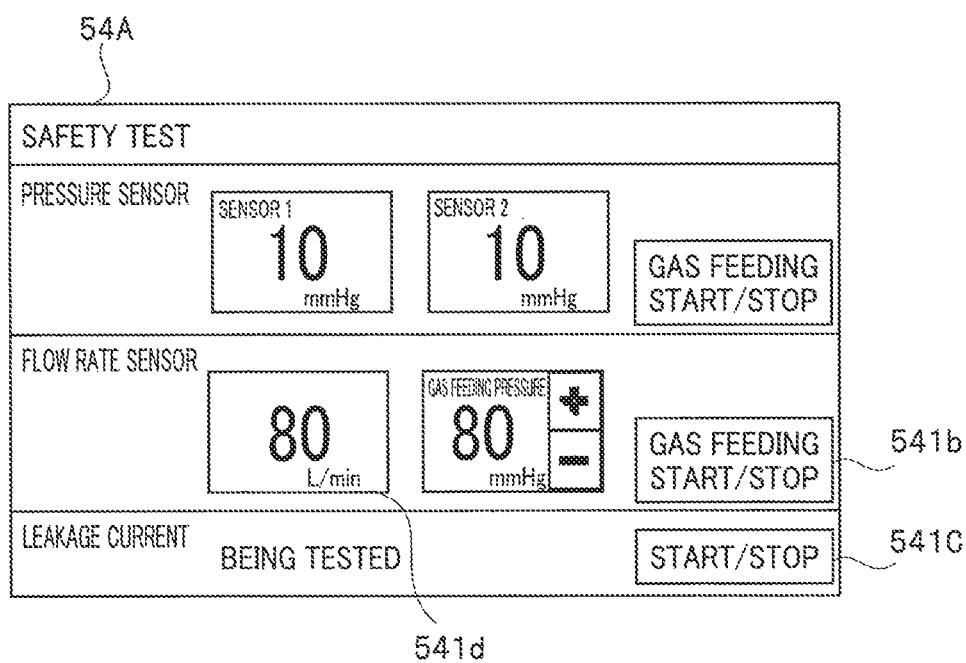
FIG. 17 is a diagram illustrating an exemplary display screen on the setting-display unit 7 in various setting.

FIG. 17 is a diagram illustrating an exemplary display screen on the setting-display unit 7 in various setting. A pressure sensor inspection display region for checking the state of a pressure sensor, a flow rate sensor inspection display region for checking the state of a flow rate sensor, and a leakage current inspection display region for checking the state of leakage current are provided on the inspection screen 54A. A continuous gas feeding button 541*b* for controlling start and stop of continuous gas feeding is provided in the flow rate sensor inspection display region. The insufflation device 1 can be operated in a continuous gas feeding state by pressing down the continuous gas feeding button 541*b*. An average flow rate during continuous gas feeding is displayed in a flow rate display part 541*d*.

A leakage current measurement button 541*c* for controlling start and stop of gas feeding operation in a maximum load state is provided in the leakage current inspection display region. Valves for controlling an opening state of the gas feeding conduit, such as the electropneumatic proportional valve 3 and the on-off valve 4 are maximumly opened by pressing down the leakage current measurement button 541*c*, and gas feeding is started in a state in which electrical power applied to the heater 151 of the gas feeding tube 15' is maximized. A load applied to the insufflation device 1 can be controlled to a maximum state without individually setting each valve.

In this manner, according to the above-described embodiment, a setting screen for various kinds of setting for performing inspection is provided so that setting of various kinds of sites in the insufflation device 1 can be performed all at once by pressing down buttons disposed on the screen, and thus inspection can be easily performed.

Ninth Embodiment

Swift detection of failure together with inspection is important for an insufflation system as a medical device. However, for a conventional insufflation system, it is impossible to determine whether failure has occurred inside the device before gas feeding control is started, and thus failure is potentially found right after start of a procedure and the procedure cannot be continued and is interrupted. Thus, the present embodiment provides an insufflation system that can sense failure inside the device before start of gas feeding control.

Figure 18:
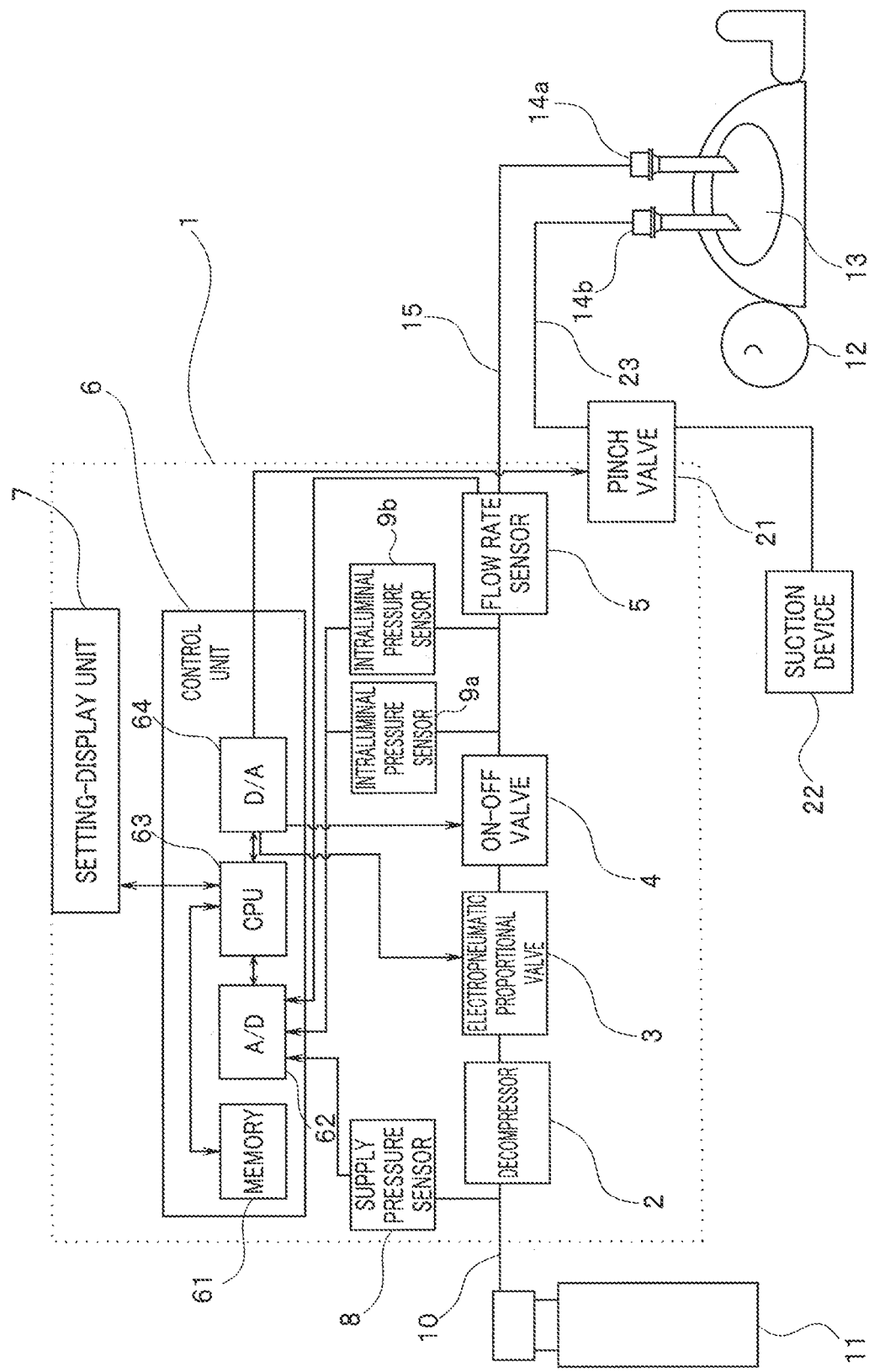
FIG. 18 is a diagram illustrating an exemplary entire configuration of an insufflation system according to a ninth embodiment.

FIG. 18 is a diagram illustrating an exemplary entire configuration of an insufflation system according to the ninth embodiment. The insufflation system according to the present embodiment has a configuration same as that of the insufflation system illustrated in FIG. 1 except that two pressure measurement units, namely, an intraluminal pressure sensor 9*a* and an intraluminal pressure sensor 9*b* are disposed as the pressure sensor 9.

Figure 19:
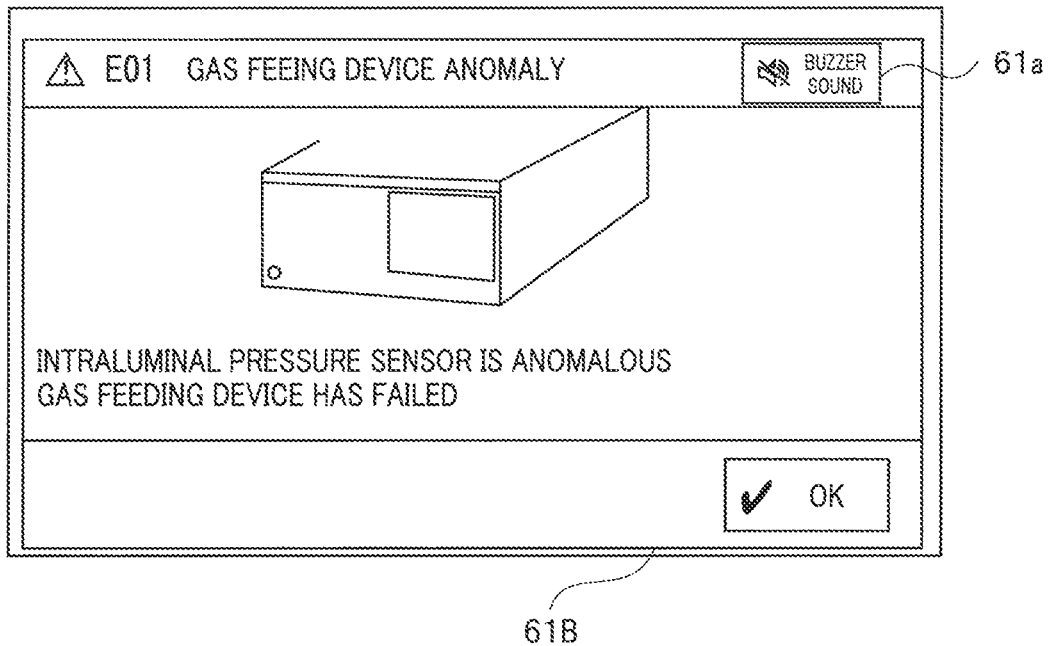
FIG. 19 is a diagram illustrating an exemplary display screen on the setting-display unit 7 in anomaly occurrence.

Upon activation of the insufflation device 1, a value measured by the intraluminal pressure sensor 9*a* and a value measured by the intraluminal pressure sensor 9*b* are inputted to the CPU 63 through the A/D 62. The CPU 63 compares the two inputted measured values. When difference between the measured values is equal to or larger than a threshold value set in the memory 61 in advance, the CPU 63 determines that failure has occurred. In this case, the CPU 63 notifies an operator or the like of an anomaly, for example, by causing the setting-display unit 7 to display an alarm screen 61B as illustrated in FIG. 19. FIG. 19 is a diagram illustrating an exemplary display screen on the setting-display unit 7 in anomaly occurrence.

Through the alarm screen 61B as illustrated in FIG. 19, the operator or the like can recognize the anomaly of the insufflation device 1 before a procedure, and thus measures such as replacement of the insufflation device 1 with an alternative machine before starting the procedure can be swiftly executed. Together with display of the alarm screen 61B, a notification of anomaly occurrence may be given by sound such as sound of a buzzer. When buzzer sound is to be generated, a buzzer sound stop button 61*a* may be provided on the alarm screen 61B to stop or mute the buzzer sound.

Tenth Embodiment

With a conventional insufflation system, an operator or the like cannot easily view records of various kinds of matters (alarm generation, notification display, and operation) occurred during control of the insufflation system. Thus, the present embodiment provides an insufflation system with which such records can be easily checked.

The insufflation system according to the present embodiment has a configuration same as that of the insufflation system illustrated in FIG. 1. Record check is performed through a setting screen on the setting-display unit 7. A screen on the setting-display unit 7 in normal operation is same as the screen illustrated in FIG. 6. When the setting button 47 of the normal operation display screen 41 is pressed down, various setting screens as illustrated in FIG. 20 are displayed on the setting-display unit 7.

Figure 20:
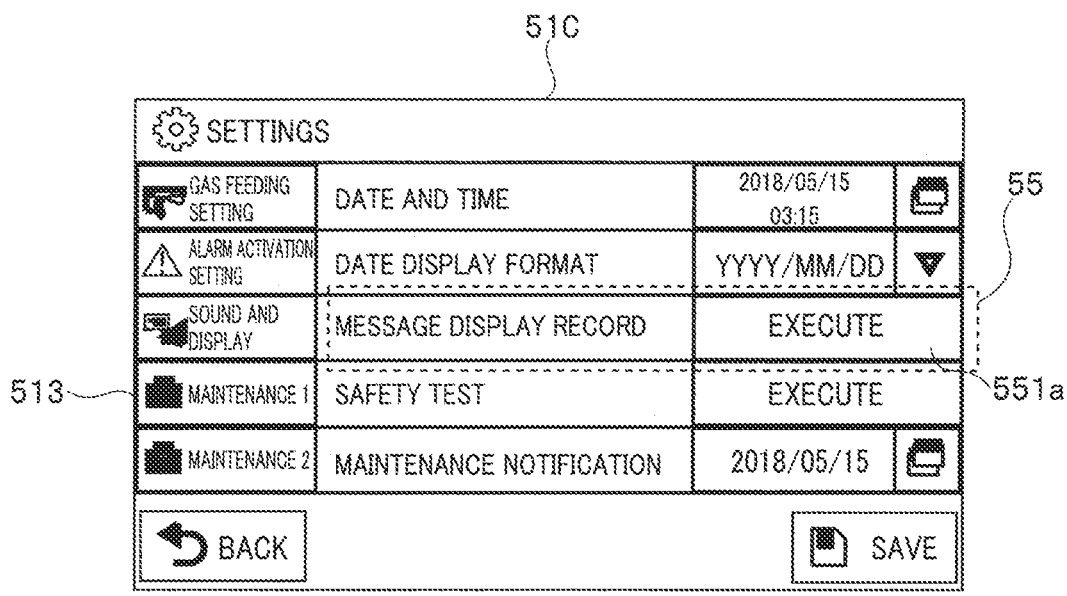
FIG. 20 is a diagram illustrating an exemplary display screen on the setting-display unit 7 in various setting.

FIG. 20 is a diagram illustrating an exemplary display screen on the setting-display unit 7 in various setting. FIG. 20 illustrates the detailed setting screen 51C for performing setting related to record check, and the detailed setting screen 51C is displayed by pressing down the "maintenance 1" button 513 among various kinds of menu buttons provided on the left side of the screen.

A record display region 55 that indicates records of displayed messages is provided on the detailed setting screen 51C. An execution button 551a is disposed in the record display region 55. A record display screen 55A as illustrated in FIG. 21 is displayed on the setting-display unit 7 by pressing down the execution button 551a.

Figure 21:
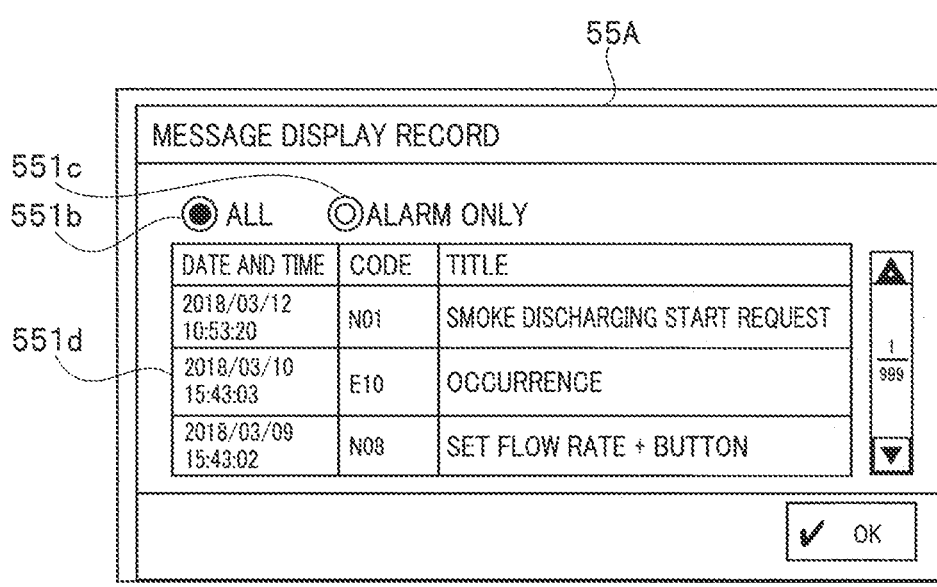
FIG. 21 is a diagram illustrating an exemplary display screen on the setting-display unit 7 in various setting.

FIG. 21 is a diagram illustrating an exemplary display screen on the setting-display unit 7 in various setting. Radio buttons 551b and 551c for selecting a kind of records to be displayed on the record display screen 55A, and a record display region 551d are provided on the record display screen 55A. When the radio button 551b is selected, various histories stored in the memory 61 are all displayed in the record display region 551d. When the radio button 551c is selected, only histories related to alarming are extracted from among various histories stored in the memory 61 and are displayed in the record display region 551d. The record display region 551d retroactively displays histories in a temporally sequential manner from a latest occurred matter.

In this manner, according to the above-described embodiment, a setting screen for displaying records of various kinds of matters (alarm generation, notification display, and operation) occurred during control of the insufflation system is provided, and records can be easily browsed by pressing down buttons disposed on the screen.

Eleventh Embodiment

As described above, it is important that, before use, an insufflation system as a medical device is inspected to check that the device has no anomaly. Thus, periodic inspection that is performed per constant duration is essential in addition to daily inspection. However, since periodic inspection is performed after a predetermined duration, an operator or the like potentially forgets a timing at which the periodic inspection is to be performed and forgets to perform the periodic inspection on a scheduled day. Thus, the present embodiment provides an insufflation system that can prevent forgetting of an inspection day by notifying the operator or the like of a scheduled day of periodic inspection.

The insufflation system according to the present embodiment has a configuration same as that of the insufflation system illustrated in FIG. 1. Record check is performed through a setting screen on the setting-display unit 7. A screen on the setting-display unit 7 in normal operation is same as the screen illustrated in FIG. 6. When the setting button 47 of the normal operation display screen 41 is pressed down, various setting screens are displayed on the setting-display unit 7, and a screen illustrated in FIG. 22 is displayed on the setting-display unit 7 by pressing down a periodic inspection setting button on the screen.

Figure 22:
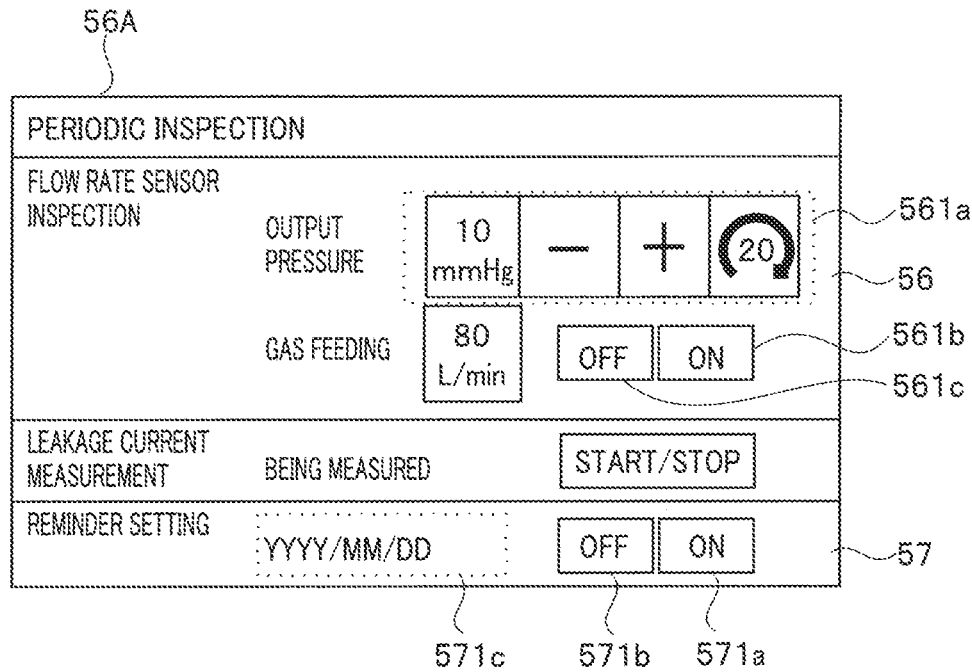
FIG. 22 is a diagram illustrating an exemplary display screen on the setting-display unit 7 in various setting.

FIG. 22 is a diagram illustrating an exemplary display screen on the setting-display unit 7 in various setting. FIG. 22 illustrates a periodic inspection screen 56A for performing setting related to periodic inspection. A flow rate sensor periodic inspection display region 56 in which matters related to flow rate sensor inspection are set and displayed, a leakage current periodic inspection display region for checking the state of leakage current, and a periodic inspection reminding setting region 57 for performing setting to remind a periodic inspection day are provided on the periodic inspection screen 56A.

An output pressure setting part 561a for setting output pressure, a gas feeding execution button 561b for starting gas feeding for periodic inspection, and a gas feeding stop button 561c for stopping the gas feeding are disposed in the flow rate sensor periodic inspection display region 56.

A reminding execution button 571a for executing reminding display of a periodic inspection day, a reminding stop button 571b for stopping the reminding display of the periodic inspection day, and a periodic inspection set day display part 571c are disposed in the periodic inspection reminding setting region 57. A set next periodic inspection execution scheduled day is displayed in the periodic inspection set day display part 571c by pressing down the reminding execution button 571a.

Figure 23:
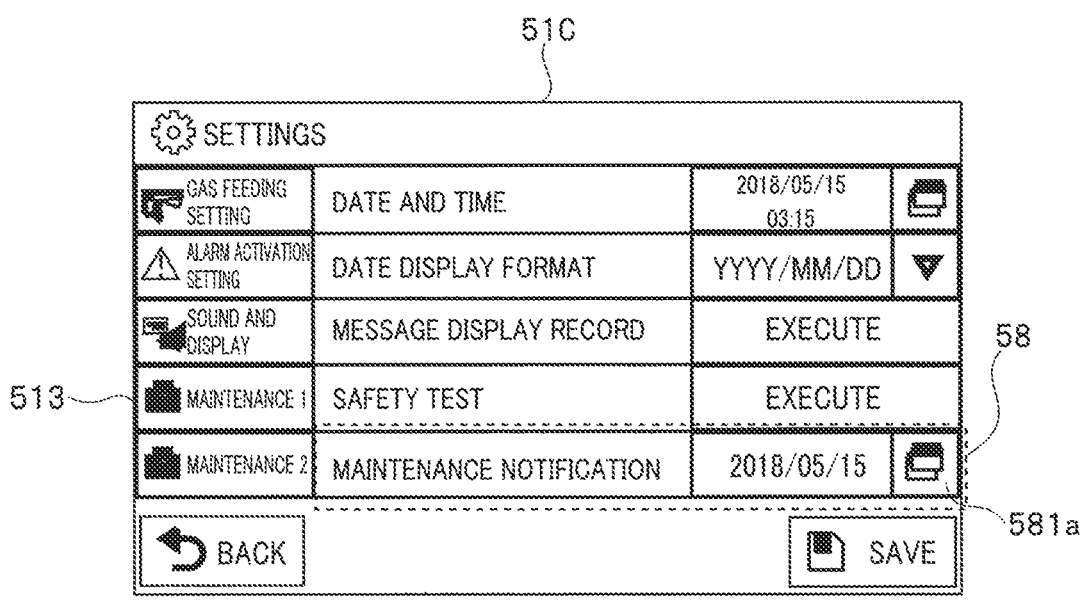
FIG. 23 is a diagram illustrating an exemplary display screen on the setting-display unit 7 in various setting.

The next periodic inspection execution scheduled day is set on a setting screen illustrated in FIG. 23. FIG. 23 is a diagram illustrating an exemplary display screen on the setting-display unit 7 in various setting. FIG. 23 illustrates the detailed setting screen 51C for performing setting of a periodic inspection day, and the detailed setting screen 51C is displayed by pressing down the "maintenance 1" button 513 among various kinds of menu buttons provided on the left side of the screen.

Figure 24:
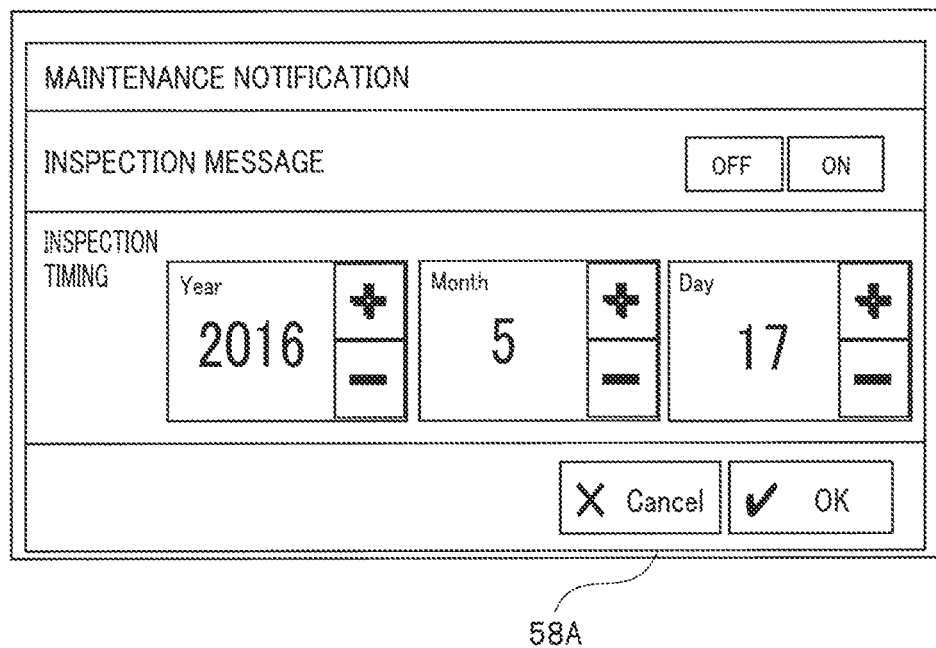
FIG. 24 is a diagram illustrating an exemplary display screen on the setting-display unit 7 in various setting.

A maintenance notification region 58 that indicates setting of a next periodic inspection day is provided on the detailed setting screen 51C. A date setting button 581a is disposed in the maintenance notification region 58. A date setting screen 58A as illustrated in FIG. 24 is displayed on the setting-display unit 7 by pressing down the date setting button 581a. When the reminding execution button 571a is pressed down, a periodic inspection set day is displayed next to the date setting button 581a.

FIG. 24 is a diagram illustrating an exemplary display screen on the setting-display unit 7 in various setting. A region for setting whether to give a notification of an inspection message and a next periodic inspection day set region are disposed on the date setting screen 58A. Reminder setting is performed by inputting and setting a date in the next periodic inspection day set region and pressing down a setting button in the inspection message region.

Figure 25:
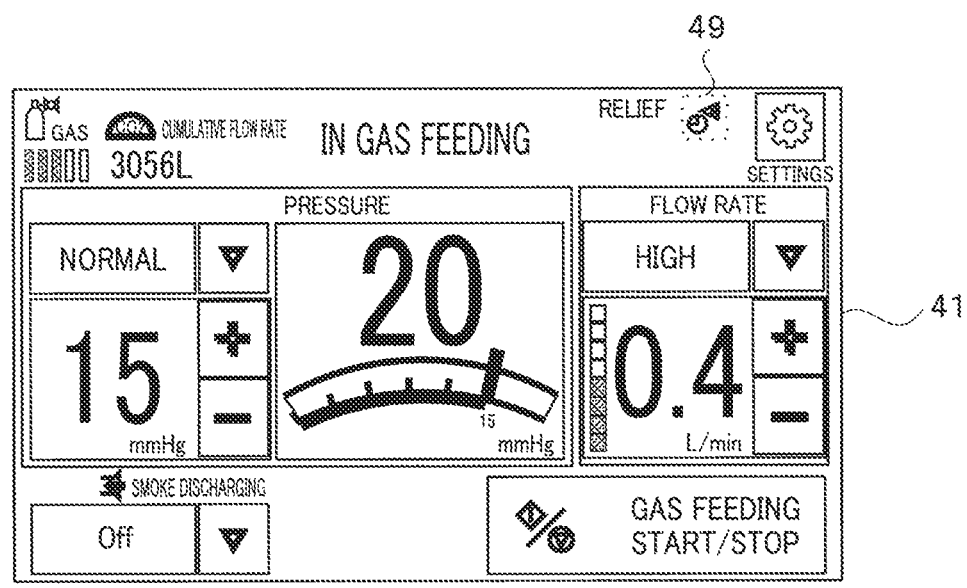
FIG. 25 is a diagram illustrating an exemplary display screen on the setting-display unit 7 in normal operation.

When reminding display is set, an icon may be displayed on the normal operation display screen 41 on a next periodic inspection day (or a day on which predetermined days are left before the next periodic inspection day). FIG. 25 is a diagram illustrating an exemplary display screen on the setting-display unit 7 in normal operation. As illustrated in FIG. 25, when reminding display is set, for example, an icon 49 at an upper-right part is displayed near the next periodic inspection day. Thus, the operator or the like can recognize that the periodic inspection day is approaching by seeing the icon 49 during a normal procedure or the like, and thus can be prevented from forgetting the inspection day.

Twelfth Embodiment

Conventionally, when an insufflation device has failed, an alternative machine is temporarily prepared to perform a procedure in many cases. In such a case, settings of the failed device need to be set to the alternative machine and used in the procedure. Typically, the setting to the alternative machine needs to be manually input and takes time and work. Thus, the present embodiment discloses an insufflation system that can easily perform setting to an alternative machine.

Figure 26:
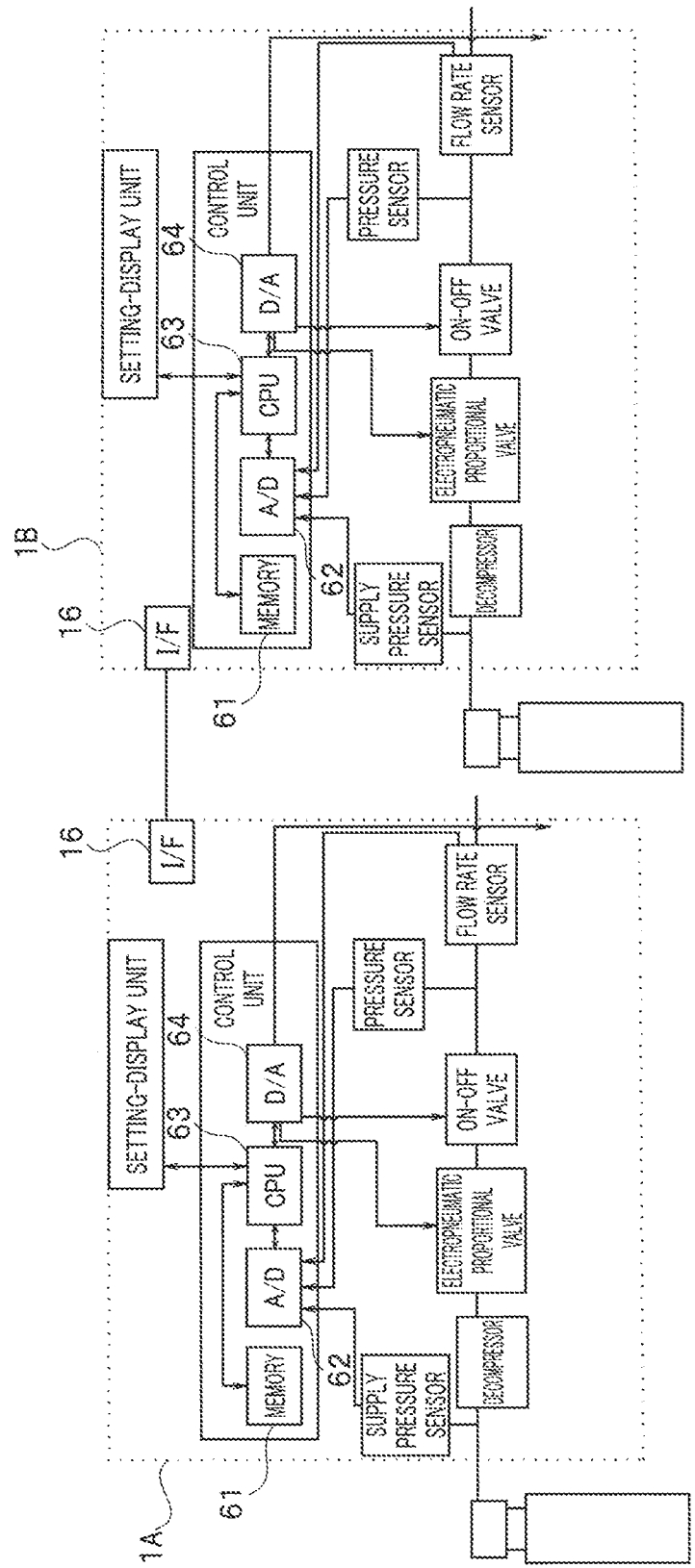
FIG. 26 is a diagram illustrating an exemplary entire configuration of an insufflation system according to a twelfth embodiment.

FIG. 26 is a diagram illustrating an exemplary entire configuration of an insufflation system according to the twelfth embodiment. An insufflation device 1A and an insufflation device 1B have a configuration same as that of the insufflation device 1 illustrated in FIG. 1 except that a communication T/F 16 is disposed, and thus any same component is denoted by the same reference sign and description of the component is omitted.

Figure 27:
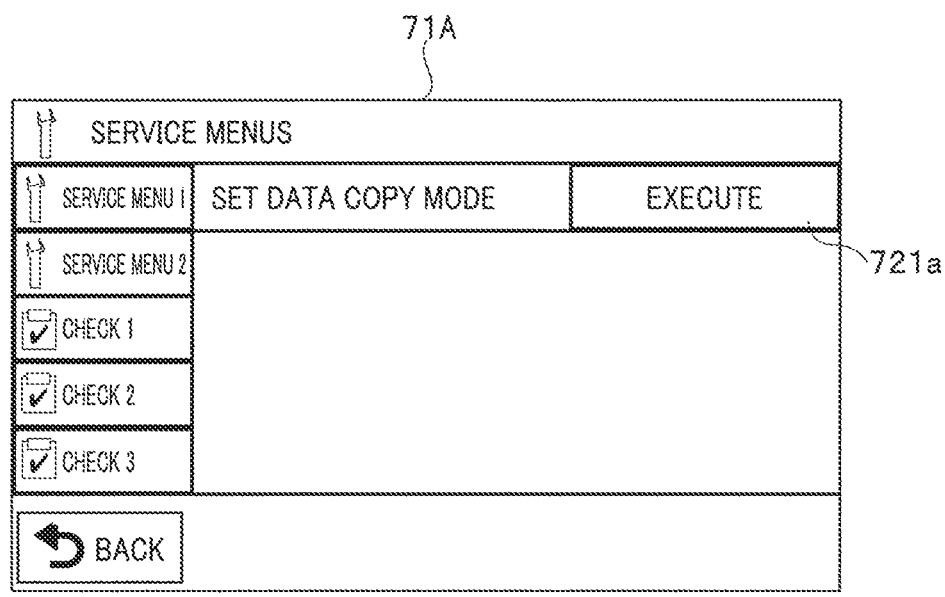
FIG. 27 is a diagram illustrating an exemplary display screen on the setting-display unit 7 in various setting.

When the communication I/F 16 of the insufflation device 1A and the communication I/F 16 of the insufflation device 1B are connected with each other through a communication cable, a data copy screen 71A illustrated in FIG. 27 is called onto the setting-display unit 7 of the insufflation device 1A. FIG. 27 is a diagram illustrating an exemplary display screen on the setting-display unit 7 in various setting. A copy execution button 721a for copying various kinds of setting data necessary for operation of an insufflation device and the like from a failed instrument to an alternative machine (connection destination instrument) is disposed on the data copy screen 71A. Various set values stored in the memory 61 of the insufflation device 1A are copied to the memory 61 of the insufflation device 1B by pressing down the copy execution button 721a. In other words, setting of the alternative machine is completed by pressing down the copy execution button 721a. In this manner, in the present embodiment, setting to the alternative machine does not need to be manually performed, and thus setting is easily completed in a short time.

The present invention is not limited to above-described examples but may include various kinds of changes and applications without departing from the scope of the invention. For example, the above description is mainly made on a case in which the present invention is an insufflation system, but the present invention is not limited to an insufflation system and may be, for example, an insufflation control method using an insufflation system, a computer program for causing an insufflation system to execute an insufflation control method under control of a computer, or a non-temporary storage medium that is readable by a computer storing the computer program.

What is claimed is:

1. An insufflation system comprising:
   a processor configured to:
      calculate a first target gas feeding flow rate based on a difference between a body cavity internal pressure and an insufflation target pressure of a body cavity;
      determine whether the first target gas feeding flow rate is lower than a threshold gas feeding flow rate; and
      in response to determining that the first target gas feeding flow rate is lower than the threshold gas feeding flow rate, feed gas at a second target gas feeding flow rate by controlling a first valve provided at a gas feeding conduit and a second valve provided at a suction conduit,
   wherein the processor is configured to cause the suction conduit to suction at a first suction flow rate, and
   wherein the second target gas feeding flow rate is obtained by adding the first suction flow rate to the first target gas feeding flow rate.

2. The insufflation system according to claim 1, wherein the threshold gas feeding flow rate is a lower limit value to which control is possible by only the first valve.

3. The insufflation system according to claim 2, further comprising:
   a third valve provided at the gas feeding conduit and configured to control a gas feeding flow rate gradually,
   wherein the first valve is provided upstream of the third valve, and
   wherein the second valve is configured to open and close.

4. The insufflation system according to claim 1, wherein the first valve is an electropneumatic proportional valve, and the second valve is a pinch valve.

5. The insufflation system according to claim 1, wherein the processor is configured to, in response to determining that the first target gas feeding flow rate is equal to or higher than the threshold gas feeding flow rate:
   control the second valve to not suction the gas from the body cavity; and
   control the first valve to feed the gas at the first target gas feeding flow rate.

6. The insufflation system according to claim 1, further comprising:
   the first valve provided at the gas feeding conduit, and configured to control a gas feeding flow rate;
   the second valve provided at the suction conduit; and
   a third valve provided at the gas feeding conduit and configured to control the gas feeding flow rate.

7. The insufflation system according to claim 6, wherein the first valve is an electropneumatic proportional valve, the second valve is a pinch valve, and the third valve is a proportional control valve.

8. The insufflation system according to claim 1, further comprising:
   the suction conduit, the suction conduit defining an aperture configured to change the first suction flow rate to a second suction flow rate that is smaller than the first suction flow rate.

9. The insufflation system according to claim 1, further comprising:
   a pressure sensor configured to sense the body cavity internal pressure,
   wherein the pressure sensor is connected with the body cavity through a pressure measurement conduit.

10. The insufflation system according to claim 1, further comprising:
    a flow rate sensor configured to measure a gas feeding flow rate; and
    a pressure sensor configured to measure the body cavity internal pressure.

11. The insufflation system according to claim 1, further comprising:
    the second valve,
    wherein the second valve is configured to open and close the suction conduit.

12. The insufflation system according to claim 1, further comprising:
    the first valve; and
    the gas feeding conduit.

13. The insufflation system according to claim 12, further comprising:
    a gas feeding source configured to feed the gas to the gas feeding conduit.

14. The insufflation system according to claim 1, further comprising:
    the second valve; and
    the suction conduit.

15. The insufflation system according to claim 14, further comprising:

a suction device configured to suction the gas through the suction conduit.

16. The insufflation system according to claim 1, wherein the processor is configured to:
   determine whether the first target gas feeding flow rate is lower than a second threshold gas feeding flow rate; and
   in response to determining that the first target gas feeding flow rate is lower than the second threshold gas feeding flow rate, determine whether the first target gas feeding flow rate is lower than the threshold gas feeding flow rate.

17. An insufflation control method comprising:
   calculating a first target gas feeding flow rate based on a difference between a body cavity internal pressure and an insufflation target pressure of a body cavity;
   determining that the first target gas feeding flow rate is lower than a threshold gas feeding flow rate; and
   in response to determining that the first target gas feeding flow rate is lower than the threshold gas feeding flow rate, feeding gas at a second target gas feeding flow rate by controlling a first valve provided at a gas feeding conduit and a second valve provided at a suction conduit,
   wherein the suction conduit is caused to provide suction at a first suction flow rate, and
   wherein the second target gas feeding flow rate is obtained by adding the first suction flow rate to the first target gas feeding flow rate.

* * * * *